United States Patent [19]
Ellmeier et al.

[11] Patent Number: 5,683,878
[45] Date of Patent: Nov. 4, 1997

[54] NEUROBLASTOMA-ASSOCIATED REGULATOR GENE

[75] Inventors: Wilfried Ellmeier, Mödling; Andreas Weith, Vienna, both of Austria

[73] Assignees: Boehringer Ingelheim International GmbH, Germany; Genentech, Inc., S. San Francisco, Calif.

[21] Appl. No.: 466,127

[22] Filed: Jun. 6, 1995

Related U.S. Application Data

[62] Division of Ser. No. 256,077, filed as PCT/EP92/02962, Dec. 19, 1992.

[30] Foreign Application Priority Data

Dec. 23, 1991 [AT] Austria .................... 2559/91

[51] Int. Cl.$^6$ .................... C12Q 1/68; C12P 19/34; G01N 33/53; C07H 21/02
[52] U.S. Cl. .................... 435/6; 435/91.2; 435/7.1; 435/7.2; 435/7.9; 536/24.3; 536/24.33; 536/23.1; 530/388.2; 530/350
[58] Field of Search .................... 435/6, 91.2, 7.1–7.9; 536/23.1, 24.3, 33; 530/388.2, 350

[56] References Cited

FOREIGN PATENT DOCUMENTS 2012311   9/1990   Canada .

OTHER PUBLICATIONS

Bader et al., "Dissociation of Suppression of Tumorigenicity and Differentiation in vitro Effected by Transfer of Single Human Chromosomes into Human Neuroblastoma Cells", *Cell Growth Differ.* 2:245–255 (May, 1991).

Benezra et al., "The Protein Id: A Negative Regulator of Helix–Loop–Helix DNA Binding Proteins", *Cell* 61:49–59 (Apr. 6, 1990).

Bernard et al., "Sequence of the Murine and Human Cellular *myc* Oncogenes and Two Modes of *myc* Transcription Resulting from Chromosome Translocation in B Lymphoid Tumors", *EMBO J.* 2:2375–2383 (1983).

Bird, A., "CpG–Rich Islands and the Function of DNA Methylation", *Nature* 321:209–213 (May 15, 1986).

Brawerman, G., "mRNA Decay: Finding the Right Targets", *Cell* 57:9–10 (Apr. 7, 1989).

Christy et al., "An Id–Related Helix–Loop–Helix Protein Encoded by a Growth Factor–Inducible Gene", *Proc. Natl. Acad. Sci. USA* 88:1815–1819 (Mar. 1991).

Davis et al., "Expression of a Single Transfected cDNA Converts Fibroblasts to Myoblasts", *Cell* 51:987–1000 (Dec. 24, 1987).

Ellis et al., "extramacrochaetae, a Negative Regulator of Sensory Organ Development in *Drosophila*, Defines a New Class of Helix–Loop–Helix Proteins", *Cell* 61:27–38 (Apr. 6, 1990).

Ellmeier et al., "Mutually Exclusive Expression of a Helix–Loop–Helix Gene and N–*myc* in Human Neuroblastomas and in Normal Development", *EMBO J.* 11:2563–2571 (Jul., 1992).

Fong et al., "Loss of Heterozygosity for the Short Arm of Chromosome 1 in Human Neuroblastomas: Correlation with N–*myc* Amplification", *Proc. Natl. Acad. Sci. USA* 86:3753–3757 (May, 1989).

(List continued on next page.)

*Primary Examiner*—W. Gary Jones
*Assistant Examiner*—Dianne Rees
*Attorney, Agent, or Firm*—Sterne, Kessler, Goldstein & Fox P.L.L.C.

[57] ABSTRACT

Disclosed is a gene situated in the region of the neuroblastoma consensus deletion 1p36.2-p36.1 which codes for a helix-loop-helix protein with the designation HEIR-1. The loss of this gene is significantly correlated with allelic tumor deletions in neuroblastomas and expression of this correlates inversely both N-myc overexpression in tumors and with N-myc expression in normal development. The cDNA and antibodies coding for HEIR-1 are used for the diagnosis of pathological conditions associated with aberration in the region of the neuroblastoma consensus deletion.

16 Claims, 10 Drawing Sheets

OTHER PUBLICATIONS

Garrell and Modolell, "The *Drosophila extramacrochaetae* Locus, an Antagonist of Proneural Genes that, Like These Genes, Encodes a Helix–Loop–Helix Protein", *Cell* 61:39–48 (Apr. 6, 1990).

Ghysen and Dambly–Chaudiere, "Genesis of the *Drosophila* Peripheral Nervous System", *Trends in Genetics* 5:251–255 (Aug., 1989).

Jones, N., "Transcriptional Regulation by Dimerization: Two Sides to an Incestuous Relationship", *Cell* 61:9–11 (Apr. 6, 1990).

Lüscher and Eisenman, "New Light on *Myc* and *Myb*. Part 1. *Myc*.", *Genes and Development* 4(12a):2025–2035 (Dec., 1990).

Martinsson et al., "Chromosome 1 Deletions in Human Neuroblastomas: Generation and Fine Mapping of Microclones from the Distal 1p Region", *Genes, Chrom. and Cancer* 1:67–78 (1989).

Murre et al., "A New DNA Binding and Dimerization Motif in Immunoglubulin Enhancer Binding, *daughterless*, *MyoD*, and *myc* Proteins", *Cell* 56:777–783 (Mar. 10, 1989).

Murre et al., "Interactions between Heterologous Helix–Loop–Helix Proteins Generate Complexes that Bind Specifically to a Common DNA Sequence", *Cell* 58:537–544 (Aug. 11, 1989).

Pochedly, C., "Neuroblastoma in infancy", in: *Neuroblastoma* (Pochedly, Ed.), London: Edward Arnold, Ltd., pp. 1–34 (1976).

Schwab et al., "Amplified DNA with Limited Homology to *myc* Cellular Oncogene is Shared by Human Neuroblastoma Cell Lines and Neuroblastoma Tumour", *Nature* 305:245–248 (Sep. 15, 1983).

Versteeg et al., "N–*myc* Expression Switched Off and Class I Human Leukocyte Antigen Expression Switched On After Somatic Cell Fusion of Neuroblastoma Cells", *Mol. Cell. Biol.* 10:5416–5423 (Oct., 1990).

Weinberg, R.A., "Tumor Supressor Genes", *Science* 254:1138–1146 (Nov. 22, 1991).

Weith et al., "Neuroblastoma Consensus Deletion Maps to 1p36. 1–2", *Genes, Chrom. and Cancer* 1:159–166 (1989).

Zimmerman et al., "Differential Expression of *myc* Family Genes During Murine Development", *Nature* 319:780–783 (Feb. 27, 1986).

Zimmerman and Alt, "Expression and Function of *myc* Family Genes", *Critical Rev. Oncogen.* 2(1):75–95 (Oct., 1990).

Goldberg et al. "Models Of Neoplasia And Their Diagnostic Implications: A Historical Perspective" Clinical Chem, 39: 2360–2374, 1993.

Martinsson et al. Genes Chromosomes And Cancer 1: 67–78, 1989.

Weith et al, Genes, Chromosomes and Cancer, 1:159–166, 1989.

| | | | | |
|---|---|---|---|---|
| 1 | AGACAATTTT | CAGCAGGAAG | AAGTAGAAAG | GATAAAATGG | ATCCTGCACC |
| 51 | ACGGGAACCT | CACAGCACCT | CACTTCTTTT | GGTTTTCTTT | CTCTTTGGGG |
| 101 | CACCTCTGGA | CTCACTCCCC | AGCATGAAGG | CGCTGAGCCC | GGTGCGCGGC |
| 151 | TGCTACGAGG | CGGTGTGCTG | CCTGTCGGAA | CGCAGTCTGG | CCATCGCCCG |
| 201 | GGGCCGAGGG | AAGGGCCCGG | CAGCTGAGGA | GCCGCTGAGC | TTGCTGGACG |
| 251 | ACATGAACCA | CTGCTACTCC | CGCCTGCGGG | AACTGGTACC | CGGAGTCCCG |
| 301 | AGAGGCACTC | AGCTTAGCCA | GGTGGAAATC | CTACAGCGCG | TCATCGACTA |
| 351 | CATTCTCGAC | CTGCAGGTAG | TCCTGGCCGA | GCCAGCCCCT | GGACCCCCTG |
| 401 | ATGGCCCCCA | CCTTCCCATC | CAGACAGCCG | AGCTCGCTCC | GGAACTTGTC |
| 451 | ATCTCCAACG | ACAAAAGGAG | CTTTTGCCAC | TGACTCGGCC | GTGTCCTGAC |
| 501 | ACCTCCAGAA | CGCAGGTGCT | GGCGCCCGTT | CTGCCTGGGA | CCCCGGGAAC |
| 551 | CTCTCCTGCC | GGAAGCCGGA | CGGCAGGGAT | GGGCCCCAAC | TTCGCCCTGC |
| 601 | CCACTTGACT | TCACCAAATC | CCTTCCTGGA | GACTGAACCT | GGTGCTCAGG |
| 651 | AGCGAAGGAC | TGTGAACTTG | TGGCCTGAAG | AGCCAGAGCT | AGCTCTGGCC |
| 701 | ACCAGCTGGG | CGACGTCACC | CTGCTCCCAC | CCCACCCCAA | GTTCTAAGGT |
| 751 | CTTTTCAGAG | CGTGGAGGTG | TGGAAGGAGT | GGCTGCTCTC | CAAACTATGC |
| 801 | CAAGGCGGCG | GCAGAGCTGG | TCTTCTGGTC | TCCTTGGAGA | AAGGTTCTGT |
| 851 | TGCCCTGATT | TATGAACTCT | ATAATAGAGT | ATATAGGTTT | TGTACCTTTT |
| 901 | TTACAGGAAG | GTGACTTTCT | GTAACAATGC | GATGTATATT | AAACTTTTTA |
| 951 | TAAAAGTTAA | CATTTTGCAT | AATAAACGAT | TT | |

FIG.3A

```
1    MDPAPREPHSTSLLLVFFLFGAPLDSLPSMKALSPVRGCYEAVCCLSERS    50
                                 ||||||||||||||||||||||
1    .............................MKALSPVRGCYEAVCCLSERS    21

51   LAIARGRGKGPAAEEPLSLLDDMNHCYSRLRELVPGVPRGTQLSQVEILQ    100
     ||||||||:|..|||||||||||||||||||||||||||||||||||||
22   LAIARGRGKSPSTEEPLSLLDDMNHCYSRLRELVPGVPRGTQLSQVEILQ    71

101  RVIDYILDLQVVLAEPAPGPPDGPHLPIQTAELAPELVISNDKRSFCH     148
     |||||||||||||||||||||||||||||||||||·||||||·|||||||
72   RVIDYILDLQVVLAEPAPGPPDGPHLPIQTAELTPELVISKDKRSFCH     119
```

FIG.3B

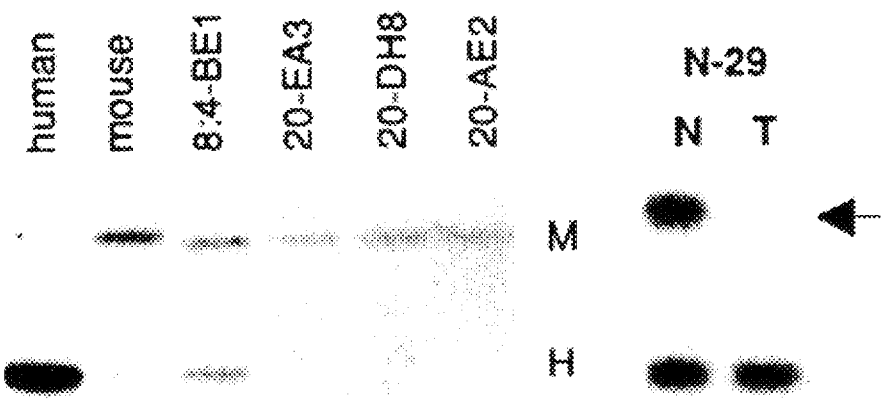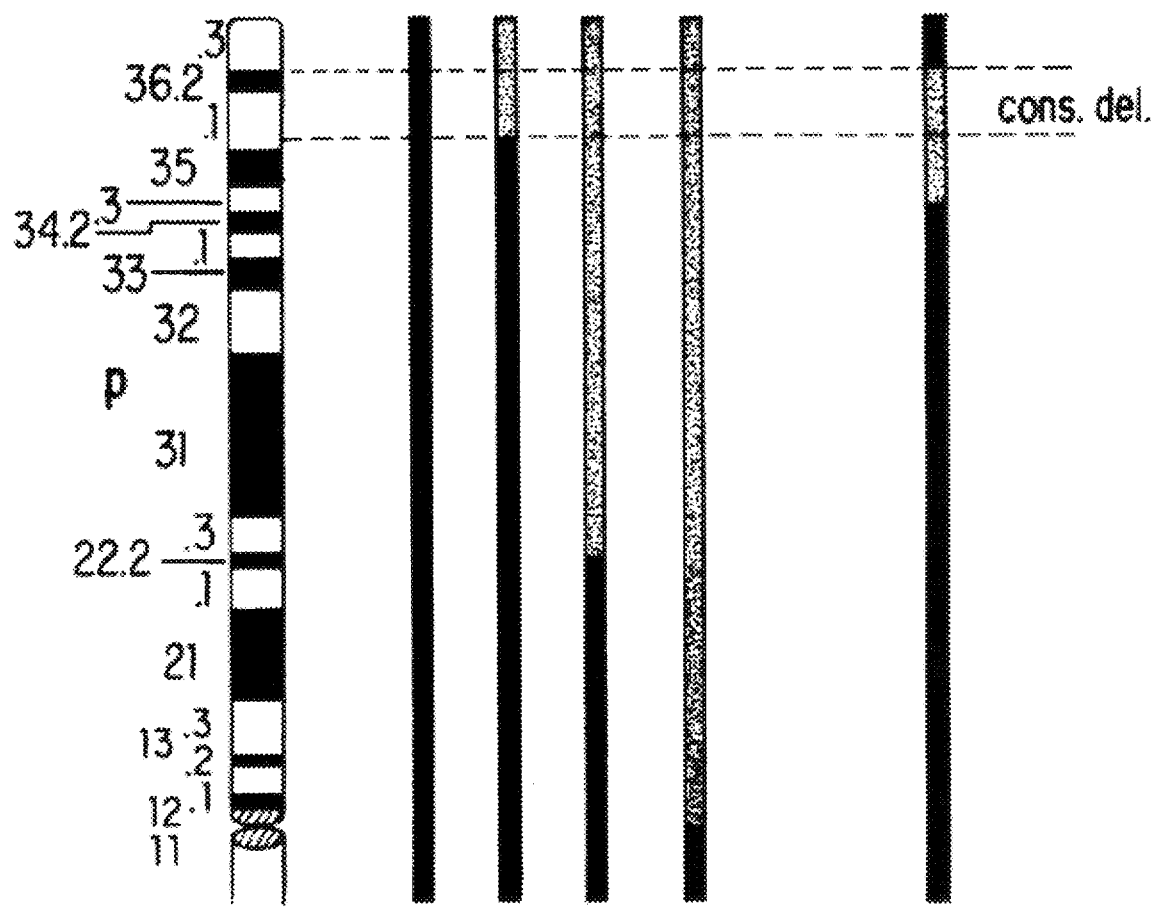
FIG.6A  FIG.6B
FIG.6C

1

NEUROBLASTOMA-ASSOCIATED REGULATOR GENE

This application is a division of copending application Ser. No. 08/256,077, filed as PCT/EP92/02962 Dec. 19, 1992.

BACKGROUND OF THE INVENTION

1. Field of the Invention

The invention relates to a gene which is affected significantly by tumour-specific deletions in human neuroblastomas and is involved in tumorigenesis.

2. Description of Related Art

A group of proteins which have been shown to act predominantly as activators of transcription share common motifs for dimerisation and DNA binding (Jones, 1990). The dimerisation domain is an amphipathic Helix-Loop-Helix (HLH)-region, and the DNA-binding is made easier by a section of basic amino acids which precede the HLH domain (Murre et al., 1989a,b). Proteins which contain this basic Helix-Loop-Helix pattern (bHLH) may form homo- and heterodimers. The modulation of the transcriptional activation by bHLH factors is brought about by another group of dimerizing proteins. This was established in the course of identifying the Id protein, a protein which also contains a Helix-Loop-Helix pattern but which lacks the basic region (HLH proteins) (Benezra et al., 1990). Id forms heterodimers with some members of the family of the bHLH transcription factors. Since it lacks the basic region which is responsible for DNA binding, heterodimers which contain Id cannot bind DNA. Therefore, bHLH proteins are most probably regulated negatively by HLH proteins such as Id. Other examples of regulatory bHLH and HLH protein interactions are the genes of the Drosophila achaete-scute-complex and the extramacrochaetae (emc) gene (Ellis et al., 1990; Garell and Modolell, 1990). These genes have a function in developing the sense organs of the peripheral nervous system (Ghysen and Dambly-Chaudiere, 1989). In general, genes which code for Helix-Loop-Helix proteins are presumed to be involved in controlling cell differentiation.

Cell differentiation is one of the processes which is affected by neoplastic transformation. Therefore, the function of genes involved in the these processes must be disrupted in tumour cells. The appearance of both dominant and recessive mutations in tumours must reflect the normal function of the affected genes as either positive or negative regulators. Up till now, Helix-Loop-Helix proteins have only been found to have effects based on dominant mutations, eg. the oncogenic activation of myc genes (Lüscher and Eisenmann, 1990; Zimmerman and Alt, 1990). However, in view of the different functions of the genes coding for HLH proteins, it should also be borne in mind that genes of this type are affected by recessive mutations and therefore have properties which correspond to the tumour suppressor genes.

Allelic deletions in specific regions of the genome, which occur significantly frequently in tumour genomes, are used as marking points for the position of tumour suppressor genes (Weinberg, 1991). In investigations of human neuroblastomas, a consensus deletion was defined in chromosome 1p36.2-p36.1 (Weith et al., 1989). The allelic loss of this section in about 80–90% of the tumours investigated led to the supposition that a gene which prevents tumours is located in this region.

SUMMARY OF THE INVENTION

The invention relates to a process for aiding in the diagnosis of neuroblastoma in humans associated with a consensus deletion of human chromosome region 1p36p12, comprising assaying a sample for the presence of a) human DNA which codes for a Helix-Loop-Helix protein (HEIR-1), wherein the nucleotide sequence of the coding region of HEIR-1 comprises the nucleotide sequence of in SEQ ID NO: 3;

b) the RNA transcribed from the human DNA; or c) the gene product expressed from that RNA;

wherein the absence of DNA having the nucleotide sequence of the coding region of HEIR-1 from at least one allele, or the RNA transcribed from the DNA, or the absence of the gene product expressed from the RNA, indicates that the sample i) comprises neuroblastoma tissue;

ii) comprises tissue of an individual with increased susceptibility to neuroblastoma compared to a normal individual; or iii) is from a neuroblastoma patient.

DESCRIPTION OF THE PREFERRED EMBODIMENTS

The aim of the present invention was to isolate a gene which prevents tumors and is located in chromosome 1p36.2-p36.1.

The following procedure was used to solve the problem: In order to identify genes in the human chromosome 1p36 region, a panel of 1p36-specific microcloned DNA probes (Martinsson et al., 1989) was used to identify CpG Islands. CpG islands represent DNA sections which are rich in CpG and 0.5–1 kbp long, which are associated with the 5' ends of numerous genes (Bird, 1986). The cytosine groups in the islands are not methylated and therefore corresponding sequences of methylation-sensitive, rarely cutting restriction enzymes are recognised. Consequently, individual probes were hybridised with pulse field electrophoresis blots of genomic DNA which had been subjected to either single or double digestion with rarely cutting restriction enzymes. Those DNA probes which were located between two CpG Islands were expected to hybridise with fragments of the same size in different single and double digestion. The probe designated p1-112B, mapped in 1pter-p36.12, showed a band of 25 kb in Bss HII, Eag I, Nae I, Nar I, Sac II and Sma I digestion (FIG. 1A). The band remained the same size in DNA which had been digested with combinations of these enzymes. Therefore, p1-112B is obviously located in a 25 kb section between two clusters of recognition sites for rarely cutting restriction enzymes (FIG. 1B).

In order to clone these clusters a genomic cosmid library was screened with p1-112B and a positive clone was isolated. The cosmid, which was designated C1-112B, contained a 37 kb genomic DNA insert. Restriction mapping of this clone with rarely cutting restriction enzymes yielded two clusters of restriction cutting sites roughly 25 kb away from each other (FIG. 2). One of the clusters was found to be contained within p1-112B probe. The other cluster was sub-cloned into a 9.0 kb EcoRI fragment (C1-112B/9.ORI). The hybridization of C1-112B/9.ORI on Southern blots with DNA which had been cut out of the clusters with the enzymes showed that the rare cutting sites in the genomic DNA are obviously not methylated and that the cluster of rare cutting sites constitutes a CpG Island. Similar results were obtained for the cluster contained in the p1-112B probe.

CpG Islands constitute the 5' end of genes and often include part of the first exon (Bird, 1986). In order to determine whether C1-112B/9.ORI recognises a transcript, a northern blot of total RNA from HeLa cells was investigated using the probe. A positive band was detected at about 1.2 kb. Then a HeLa cDNA library was searched using C1-112B/9.ORI. Two different cDNA clones of different lengths were isolated. The two clones were sequenced; sequence analysis yielded an identical sequence for both clones, apart from the fact that 200 bp was missing from the shorter clone at the 5' end. The longer clone was designated HEIR-1 and used for subsequent experiments. Its sequence (SEQ ID NO: 1) comprises 982 nucleotides and contains a single open reading frame, beginning with a start codon at position 37 and ending with a TGA stop codon at position 481. In the reading frame with the first ATG, an additional possible start codon was found at position 124. The 3'-untranslated region contains a poly(A) signal at position 971. An ATTTA motif, which was shown to be responsible for the short half life of the mRNA (Brawerman, 1989), was also found in an AT-rich section of the 3'-untranslated part of the message.

Since no stop codon was found in the reading frame 5' from the first start codon, it was not ruled out initially that the reading frame extends further in the 5' direction.

Direct sequencing of the region 5' from the ATG codon at position 124 of the cosmid C1-112B showed that the sequence of the HEIR-1 cDNA clone differs from the genomic DNA in this section. Direct sequence analysis of the 5' region (nucleotide 1–123) from the cDNA clone showed no homology with the genomic locus. It was therefore assumed that this DNA section of the HEIR-1 cDNA clone is a cloning artefact.

The genomic DNA fragment p1-112B is located on chromosome 1pter-p36.12. In order to confirm the position of the HEIR-1 gene, a series of (HumanXMouse) microcell hybrids (Martinsson et al., 1989) were used for mapping by means of Southern blot analysis (Southern Mapping). The hybrid cell lines each contain the human chromosome 1 with various deletions of the 1p arm as the only human material on a mouse background. The HEIR-1-cDNA was tested on a Southern blot containing EcoRI-digested DNA of the four hybrid cell lines (FIG. 6). A positive human fragment was found only in the DNA of the particular hybrid which contained an intact chromosome 1, but not in any of the hybrids which had deletions in the 1pter-p36.12 region. From this, it could be concluded that HEIR-1 is situated in the same chromosome regions as the genomic probe which was initially used to identify the CpG Island, and that the gene found is consequently the one which was being sought.

The deletion "break-off" point of the hybrid cell line 20-EA3 characterises the proximal limit of the neuroblastoma consensus deletion (Martinsson et al., 1989; Weith et al., 1989). Since HEIR-1 is located distally of this break-off point an investigation was also made to see whether the gene locus is contained within the limits of the consensus deletion. For this purpose, a neuroblastoma tumour designated N-29 (Weith et al., 1989) was investigated with an allelic deletion, the distal break-off point of which, marks the distal limit of consensus deletion. Using a restriction fragment length polymorphism (RFLP), an allelic deletion in the HEIR-1 locus of this tumour was detected. This constituted proof that HEIR-1 is located in the neuroblastoma consensus deletion.

The present invention relates to a new human DNA sequence which is located in the neuroblastoma consensus deletion 1p36.2-p36.1 and which contains the region coding for a Helix-Loop-Helix protein designated HEIR-1.

According to one aspect of the invention the DNA is genomic DNA.

According to another aspect of the invention the DNA is a cDNA.

The open reading frame of the HEIR-1 cDNA codes for a protein of 119 amino acids which contains a Helix-Loop-Helix motif. The coding region of the cDNA and the derived polypeptide sequence are shown as SEQ ID NO: 3 and SEQ ID NO: 4. (The open reading frame found in the isolated cDNA clone which has the sequence shown in SEQ ID NO: 1 would code for a polypeptide of 148 amino acids; the correspondingly derived amino acid sequence is shown in SEQ ID NO: 2.) Sequence comparison with members of the family of the HLH transcription factors yielded 95.8% identity with the murine HLH 462 (Christy et al., 1991) over all 119 amino acids of HLH 462 (FIG. 3B). The differences in amino acids between HEIR-1 and the murine HLH 462 protein are obtained by replacing 5 non-polar amino acids with 5 polar amino acids. These changes are outside the HLH motif. The N-terminal 29 amino acids of the protein derived from the cDNA clone are not contained in the mouse protein (FIG. 3B). It was therefore assumed that the second ATG at position 124 coincides with the start codon of HLH 462, i.e. the first ATG is skipped over and the second ATG is the correct start codon of HEIR-1. This assumption was confirmed by direct sequencing of the genomic locus (see above).

The HLH motif of HEIR-1, like that of HLH 462 (Christy et al., 1991), shows clear homology with the HLH motifs of Id and the drosophila emc protein. In particular, 11 of the 16 amino acids of the second Helix are conserved between HEIR-1, Id and emc (FIG. 4). Like Id, emc and HLH 462, HEIR-1 lacks a basic region which is necessary for specific DNA binding and in which is found in bHLH proteins. However, a clear similarity was also found with the HLH motifs of bHLH proteins such as MyoD (Davis et al., 1987), c-myc (Bernard et al., 1983) and E47 (Murre et al., 1989a).

The availability of HEIR-1-cDNA presupposes the production of HEIR-1 in larger quantities as a recombinant protein. Production takes place in suitable prokaryotic or eukaryotic host organisms, e.g. *E. coli*, yeast or cells of higher organisms. The techniques used to produce recombinant polypeptides are well known to those skilled in the art; vectors, control sequences and so on which are suitable for the particular expression host can be found in the relevant text books (eg. Sambrook et al., 1989, Molecular Cloning a Laboratory Manual. Cold Spring Harbor Laboratory).

The invention thus relates, according to a further aspect, to recombinant DNA molecules containing the DNA coding for HEIR-1 as well as expression control sequences functionally connected therewith, and the host organisms transformed therewith.

The method of restriction mapping is used to determine whether the complete HEIR-1 gene is contained in the isolated cosmid clones. In order to do this, cosmid DNA is cut with restriction enzymes, gel-fractionated, transferred to membranes and hybridized with the HEIR-1 cDNA. It is taken as proof of completeness if the cosmid DNA has all the restriction fragments which are homologous to the cDNA. Other genomic clones can be obtained from the genomic libraries by screening with the cDNA according to the invention. The 5'-regulatory region was determined by sequencing with the aid of a primer which was complementary to the 5' region of the coding gene section. Sequencing was carried out in the genomic DNA clone C1-112B/9.ORI. The sequence, including the start codon, is shown in SEQ ID NO: 5.

The invention further relates to the recombinant HEIR-1 protein.

The availability of the protein makes it possible to prepare anti-HEIR-1 antibodies, preferably monoclonal anti-HEIR-1 antibodies.

The present invention thus further relates to antibodies against HEIR-1, preferably monoclonal antibodies, as well as hybridoma cells which produce such antibodies, and processes for preparing them.

The preparation of monoclonal antibodies is familiar to those skilled in the art; suitable methods are described in the relevant text books, eg. Harlow and Lane, 1988). The preparation is based essentially on the method described by Köhler and Milstein, 1975, in which animals such as mice are immunized with the antigen, B-lymphocytes from the immunized animals are fused with myeloma cells and the antibodies are obtained from the resulting hybridomas.

Since the HEIR-1 gene is located in a genomic region which is frequently affected by allelic deletions in neuroblastomas, a number of neuroblastomas have been searched for deletions of the HEIR-1 locus. Using an Apa I restriction fragment length polymorphism (RFLP) test for this locus, a so-called LOH (loss of heterozygosity) analysis was carried out. Southern blots prepared with DNAs from 16 different neuroblastomas and the DNAs from the corresponding normal tissue, digested with Apa I, were investigated using HEIR-1-cDNA as the probe.

Heterozygosity of the locus was found in the DNA of 11 different normal tissues. Of these 11 cases, 7 exhibited a tumour-specific loss of an allele. Among these 7 tumours there were two which had been shown to have allelic deletions which constituted the proximal and distal limits of the neuroblastoma consensus deletion (FIG. 8) (Weith et al., 1989). Since the HEIR-1 probe in both cases showed a loss of heterozygosity, the loss of the locus could obviously be associated with the consensus deletion.

In order to detect whether the HEIR-1 gene is transcribed tissue-specifically, Northern analysis was carried out. The HEIR-1 cDNA was used first as a probe in order to investigate Northern blots containing poly(A)+RNA from nine different adult human organs (FIG. 5A). Strong signals were obtained in RNA taken from lung, kidney and adrenal gland; this indicated that the gene in these tissues is transcribed in large amounts. In placenta, muscle, liver and pancreas the message was present only to a small degree. No transcript of the gene could be detected in the brain. Two positive clones were obtained from a fetal brain library. The sequence determined from one of the two clones differed from the sequence shown in the sequence data insofar as this sequence contained an additional 100 nucleotides. Since these additional nucleotides are located between two typical splice consensus sequences, the clone found would appear to be derived from RNA which has not been completely processed; however, one cannot rule out the possibility that this heterogeneity has a functional relevance. Thus, by definition, the HEIR-1 sequences according to the invention also include sequences which differ from the ones shown in the sequence data by having additional sequence sections which can be ascribed to alternative splicing.

The adrenal gland is the primary target organ for neuroblastoma tumours. More than 65% of tumours develop from cells of the medulla of the adrenal gland (Pochedly, 1976; Russell and Rubinstein, 1989). HEIR-1 expression was investigated in medulla cells once it had been established that HEIR-1 is expressed strongly in the adrenal gland. For this purpose, the HEIR-1 probe was hybridised with Northern blots containing poly(A)+RNA from cortex and medulla of the bovine adrenal gland. In preliminary tests zoo blot analysis had shown that HEIR-1 is highly conserved in all mammalian species; bovine tissue proved as suitable as any other mammalian tissue. It was shown that HEIR-1 expression in the adrenal gland is found predominantly in the medulla, whereas the cortex exhibits virtually no signal. This result was also confirmed by positive signals from cultured chromaffin cells from the medulla of rat adrenal glands (PC12 cells).

In view of the high degree of homology between HEIR-1 and murine HLH 462 and the easier availability of murine tissue compared with human tissue, the transcription pattern of the human probe was investigated in murine tissue in order to be able to develop a murine model for the tissue-specific function of the gene in humans. Investigation of a Northern blot of poly(A)+RNAs from various murine tissues showed high transcript concentrations in the lung, liver and kidney, whereas the transcription in the adipose tissue, heart, spleen, brain and muscle was significantly less (FIG. 5B). No transcript could be detected in the testes. The transcription patterns in the two different species were thus not entirely comparable; in particular, the different expression of HEIR-1 in the liver showed that the two organisms did not have identical distribution of the gene product.

After it had been shown that the HEIR-1 gene is located in the neuroblastoma consensus deletion, transcription of HEIR-1 in neuroblastomas was investigated. Northern blots containing poly(A)+RNA from 12 different neuroblastoma cell lines were investigated with HEIR-1 cDNA as probe. For this purpose the high expression of the gene in the adrenal glands was regarded as a normal control, as it is known that more than 65% of all neuroblastomas originate in this organ. As shown in FIG. 7, 10 of the tumour RNAs exhibited very weak HEIR-1 signals, indicating a specific reduction in the gene activity. Strong signals were found only in the RNA of the tumour cell line SK-N-SH and a subclone thereof, SH-EP. In spite of the two different RNA concentrations, all tumour RNAs showed bands of the same size as were observed in normal tissues. This indicates that the HEIR-1 mRNA should not be affected by any tumour-specific structural rearrangement.

The amplification and overexpression of the oncogene N-myc is characteristic of numerous neuroblastomas, particulary at advanced stages (Zimmerman and Alt, 1990). In order to determine how the two different levels of HEIR-1 expression are connected with the over expression of N-myc, HEIR-1 was removed from the Northern blots and the blots were again hybridised with the Nb-1 probe which is specific for the human N-myc gene (Schwab et al., 1983). Of the 12 tumour cell lines, eight exhibited a very strong signal which indicated over expression of N-myc (FIG. 7). When the HEIR-1 transcription was compared with the over expression of N-myc in the relevant tumour cell lines, a clear correlation was found: those tumour cell lines which exhibited high concentrations of N-myc had a very low level of HEIR-1 mRNA. In the two cell lines in which this correlation was not found, the low HEIR-1 transcription possibly correlates inversely with an over expression of c-myc, as the rehybridization of the Northern blot with a c-myc-specific probe indicates (see FIG. 7); a clear correlation of HEIR-1 generally with genes of the myc family still requires definitive confirmation.

Within the scope of the present invention it was further found that the expression of HEIR-1 and N-myc are mutually exclusive in normal development: as for the proto-oncogene N-myc, it is known to be expressed in normal embryonic development (Zimmerman et al., 1986). After it was shown by isolation of cDNA clones from the fetal brain that HEIR-1 is expressed in embryos, investigations were carried out to discover whether there might possibly be an inverse correlation between the expression of HEIR-1 and N-myc, not only tumour cells but in normal development as well. For this purpose, both genes were analysed for their expression throughout development by in situ hybridisation on murine tissue and compared.

The supposition that the HEIR-1 gene is involved in tumorigenesis was thus confirmed by the investigations of HEIR-1 transcription in normal tissues and in neuroblastoma cells, carried out within the scope of the present invention, and by the observation that the HEIR-1 transcription levels in human neuroblastomas and in normal tissues during development are inversely correlated with an overexpression of N-myc.

According to a further aspect, the present invention relates to the use of HEIR-1 DNA sequences or parts thereof and antibodies against HEIR-1 for the clinical diagnosis of pathological conditions which are associated with an aberration in the neuroblastoma consensus deletion area 1p36.2-p36.12 or for diagnosing a predisposition to such diseases. By these diseases is meant primarily tumour diseases, particularly neuroblastomas.

The fact that the HEIR-1 cDNA recognises an RFLP in Apa I-digested genomic DNA which makes it possible to identify chromosome 1 homologues is the prerequisite for recognising allelic deletions which are specific to 1p36.2-p36.12 and which occur, for example, in neuroblastomas. Compared with known RFLP probes (Fong et al., 1989; Weith et al., 1989) the information which is obtained using the DNA according to the invention as probe is of great significance in the diagnosis of neuroblastoma, as an RFLP test based on the use of the probe according to the invention will detect a gene which is directly connected with the tumorigenesis. Within the scope of the tests carried out, a high degree of heterozygosity was detected in neuroblastoma patients; in view of this high degree of heterozygosity, a test based on the probe according to the invention is more reliable than the known RFLP tests which operate with probes which detect a lower level of heterozygosity.

In the course of the RFLP tests carried out, it was found that the use of the complete coding region of the HEIR-1 cDNA gives reliable results. However, apart from the complete sequence, it is also possible to use parts thereof which recognise the RFLP. The suitability of cDNA fragments can be established by comparing any desired fragments, which are preferably at least about 200 bp long for the purposes of obtaining a detectable signal, with the complete probe in terms of its ability to recognise the RFLP. Such fragments may, for example, be prepared by PCR amplification as a preliminary step.

The use of the HEIR-1 cDNA probes according to the invention for diagnosing 1p36.2-p36.12 deletions in tumours is carried out according to standard methods: after the removal of a tumour, the DNA, and in parallel thereto, DNA from healthy tissue or peripheral blood from the patient is prepared, cut with Apa I and fractionated by gel electrophoresis. After Southern transfer onto membranes it is hybridised with the probe according to the invention (the probe need not correspond exactly to the cDNA sequence; it is sufficient if it corresponds to a degree which, under the particular conditions selected, makes it possible to carry out hybridisation with the DNA, or possibly RNA which is to be analysed). The probe may carry any desired labelling which can be made visible and will not affect the hybridisation qualities of the probe; examples of conventional labels are radioactivity as well as digoxigenin or biotin in conjunction with fluorescence or alkaline phosphatase reaction.

The RFLP test for a HEIR-1 deletion is conveniently carried out in parallel to the investigation into amplification of the N-myc gene. Alternatively to DNA, RNA from tissues which are to be investigated can be analysed by means of the DNA probe according to the invention, e.g. by means of conventional Northern blots.

Anti-HEIR-1 antibodies are used for primary diagnosis of pathological conditions associated with aberrations in the region 1p36.2-p36.12 and in those cases where N-myc amplification and/or HEIR-1 deletion cannot be detected or cannot be clearly shown. The assays using the antibodies are generally conventional immunoassays in which the probe is intended to form a binary or ternary complex between the HEIR-1 gene product, or possibly a fragment thereof, with one or more antibodies, one of which has a detectable label. The use of an antibody with exclusive specificity for HEIR-1, ie. an antibody which does not cross-react with HEIR-1 related proteins, makes it possible to determine HEIR-1 specifically in tissues.

In the light of tests carried out recently (Bader et al., 1991) it is assumed that the chromosome 1p-Arm contains an element which has the ability to revert the tumour phenotype into an untransformed phenotype. Since HEIR-1 maps into the neuroblastoma consensus deletion situated in this region, it obviously satisfies one of the essential pre-requisites for a gene which is involved in the formation of neuroblastomas, on the basis of its functional loss. A further indication that HEIR-1 is connected both with differentiation and also with the tumorigenesis of neuroblastomas arises from its expression pattern: in contrast to the adult brain, it is transcribed in the embryonic brain, which indicates that the gene is active in tissues which are engaged in development and therefore contributes to processes of differentiation. Another essential aspect of HEIR-1 genetic activity, on the basis of which it can be assumed that HEIR-1 acts as a tumour suppressor gene, is its striking transcription in the medulla of the adrenal gland, by contrast with minimal transcription in the majority of neuroblastomas. This fact is particularly remarkable because the adrenal gland is the target tissue of most neuroblastomas. Since it is generally recognised that tumours at an advanced stage and their metastases originate predominantly from medullary cells of the adrenal gland, it can be concluded from the present findings that the activity of HEIR-1 in tumours is specifically reduced.

Six of the neuroblastoma cell lines investigated were examined in vivo for their ability to form tumours, 5 of them formed tumours in immunodeficient mice. Comparison of the tumorigenicity with the HEIR-1 expression shows a striking coincidence of normal genetic activity with the inability to form tumours. From this it can be concluded that HEIR-1 has an essential function in suppressing tumours in vivo.

The traces of transcripts detected which are found in the majority of tumour cell lines presumably result from the greatly reduced expression of the alleles of the gene remaining the tumour cells. Earlier cytogenetic and molecular investigations indicate that at least one copy of the region which includes HEIR-1 would appear to be retained in the tumour cell lines used (eg. GI-ME-N; Martinsson et al., 1989; N-16: Weith et al., 1989). It is not known at present whether regulation of the HEIR-1 transcription or post-transcriptional changes are responsible for the small amounts of HEIR-1 mRNA. To find out, the 5' control regions of the gene are investigated.

Another indication of the involvement of HEIR-1 in neuroblastoma tumorigenesis is provided by comparison of the HEIR-1 transcription with N-myc expression in neuroblastomas. It is known that N-myc is specifically over-expressed in a high proportion of neuroblastomas at an advanced stage and that it correlates positively with tumour progression and metastases formation. Consequently, from the inverse correlation between HEIR-1 and N-myc activity, it can be deduced that HEIR-1 plays a functional role in malignant transformation. The mechanism of the correlation has not yet been explained; however, in view of the present results, it would seem likeliest that the reduction in HEIR-1 expression as a tumour-specific event precedes the N-myc over-expression and this gene possibly negatively regulates the transcription of N-myc by, an as yet unknown, method. The structure of the gene, which is characteristic of a negatively regulated gene, would also be in keeping with such a mechanism. Without wishing to be tied down to this theory, the dimerization of HEIR-1, occurring in healthy tissue, with a genetic product potentially acting as an oncogene could inhibit the latter. The loss of the HEIR-1 gene could lead to constitutive activation of the oncogene and hence initiate a tumour. Another indication of negative regulation is provided by the mutual exclusion of the activity of HEIR-1 and N-myc in developing tissues. The results of the investigation of the embryonic fore-brain having been particularly suggestive: although HEIR-1 and N-myc are expressed at the same stage of development in the same type of tissue, namely the neuroectoderm, they are active in separate but adjoining areas. The mutual exclusion was particularly noticeable because of sharp boundaries between the different sections expressing HEIR-1 and N-myc, respectively.

In order to confirm the function of HEIR-1 as a tumour suppressor gene, tests are carried out by means of which the influence of a normally expressed HEIR-1 gene (ie. corresponding, in terms of quantity and sequence, to the HEIR-1 expressed in healthy normal tissue) can be observed in tumour cells. For expression analyses of this kind, tumour cell lines, eg. the neuroblastoma cell lines IMR-32, Vi856 and SK-N-SH, are transformed with vectors which are replicable in mammalian cells and are capable of being selected, wherein said vectors contain the cDNA coding for HEIR-1 under the control of a strong promoter. The cells are then investigated for their phenotype, particularly their malignancy. The loss of the malignant phenotype defines the HEIR-1 gene as a tumour suppressor gene by means of which pathological conditions which involve malfunction of the gene can be treated therapeutically. Such conditions include, in particular, those tumour diseases which are diagnosed by means of the HEIR-1 probes. These are primarily neuroblastomas in which a direct correlation between HEIR-1 and tumorigenesis has been detected, as well as other tumours which have a corresponding abberation in chromosome 1p36.2-p36.1 (there are indications that other forms of cancer have significant chromosomal abberations in the same region of chromosome 1 as neuroblastoma, such as hepatoma, malignant melanoma, glioblastoma, Merkel's cell carcinoma and breast cancer). Confirmation of the fact that HEIR-1 is involved in the formation of these tumours can be obtained by carrying out the investigations which were performed for neuroblastoma using HEIR-1, including the functional expression analyses, in cells which originated from the tumours in question.

The principle of therapeutic treatment consists in administering a therapeutically effective quantity of HEIR-1 to the body or causing it to be expressed in the body, i.e. supplying the body with the genetic product or, in the course of gene therapy, the gene, i.e. within the scope of whole body treatment. The gene as part of a vector under the control of a tissue-specific promoter, is introduced into the body using gene transfer procedures, i.e. using ligands which bind to tissue-specific receptors (a method of this kind which uses transferrin conjugates with DNA for receptor-mediated endocytosis is described in EP 388 758). The gene is then expressed in the target tissue. In the treatment of neuroblastomas, suitable gene transfer agents are ligands for receptors which are expressed by cells originating from the neural crest, e.g. transferrin (experiments have shown that DNA associated with transferrin is efficiently taken up into such cells). Since the transcription patterns obtained in the course of the present invention have shown tissue specificity in HEIR-1 transcription, basically tissue specificity is sought within the scope of gene therapy. This is also true when using retroviral vectors in which the tissue specificity of the gene construct used is of major importance, particularly as a result of possible dominance of the retroviral promoter. Conveniently, the HEIR-1 promoter is used for gene constructs for use in gene therapy, in order to achieve, as far as possible, tissue specificity and the amount of HEIR-1 expression corresponding to expression in normal tissue. To achieve more intense expression, multiple copies of promoter sub-fragments may possibly be contained in the construct.

BRIEF DESCRIPTION OF THE DRAWINGS

FIG. 1A shows the pulse field gel hybridization of microclone p1-112B. FIG. 1B is a schematic representation of the genomic region characterized by p1-112B. The probe is illustrated by a shaded horizontal bar.

FIGS. 3A and 3B. FIG. 3A shows the nucleotide sequence of the cDNA clone known as HEIR-1 (SEQ ID NO: 1). FIG. 3B shows a comparison of the derived amino acid sequences of HEIR-1 (SEQ ID NO: 2) with murine HLH462 (SEQ ID NO: 4) protein.

FIG. 5A shows northern blots of poly(A)+RNA from 9 different adult tissues hybridized to a HEIR-1 cDNA probe. FIG. 5B shows northern blots of poly(A)+RNA from adult mouse tissue, hybridized with a human HEIR-1 probe. FIG. 5C shows a northern hybridization of the HEIR-1 cDNA probe with poly(A)+RNAs of cortex bovine adrenal gland, medulla of bovine adrenal gland and rat PC12 cells;

FIGS. 6A, 6B and 6C. FIG. 6A shows a Southern blot of EcoRI-digested DNA from different (MouseXhuman) microcell hybrids hybridized with a $^{32}$P-labeled HEIR-1 cDNA. FIG. 6B shows an analysis of the loss of heterozygosity (LOH) at the HEIR-1 locus of the neuroblastoma patient N-29. FIG. 6C shows a diagram demonstrating the localization of the HEIR-1 gene in the neuroblastoma consensus deletion.

The invention is illustrated by means of the Examples which follow:

Materials and Methods

Cell lines and materials obtained from neuroblastoma patients.

The following neuroblastoma cell lines were used: Vi856; N15, N16 (Weith et al., 1989), SK-N-SH, SH-EP (Biedler et al., 1973), GI-ME-N (Donti et al., 1988), GI-LI-N, GI-CA-N (Longo et al., 1988), LS (Rudolph et al., 1991), Kelly (Schwab et al., 1983), IMR-32 (Tumilowicz et al., 1970), NMB (Balaban-Malenbaum and Gilbert, 1977), LAN-5 (eg. Minth and Dixon, 1990). All the cell lines were kept in RPMI with 10% FCS, 1% penicillin/streptomycin and 4 mM L-glutamine. The hybrid (MouseXHuman) cell lines 8:4-BE1, 20-EA3, 20-DH8 and 20-AE2 have been described by Martinsson et al., 1989. Rat PC 12 cells (Greene and Tischler, 1976) were grown in DMEM containing 15% equine serum, 1% penicillin/streptomycin and 4 mM L-glutamine. Tumour tissue and peripheral blood taken from patients designated N-15 and N-29 have been described by Weith et al. (1989).

Figure 2:
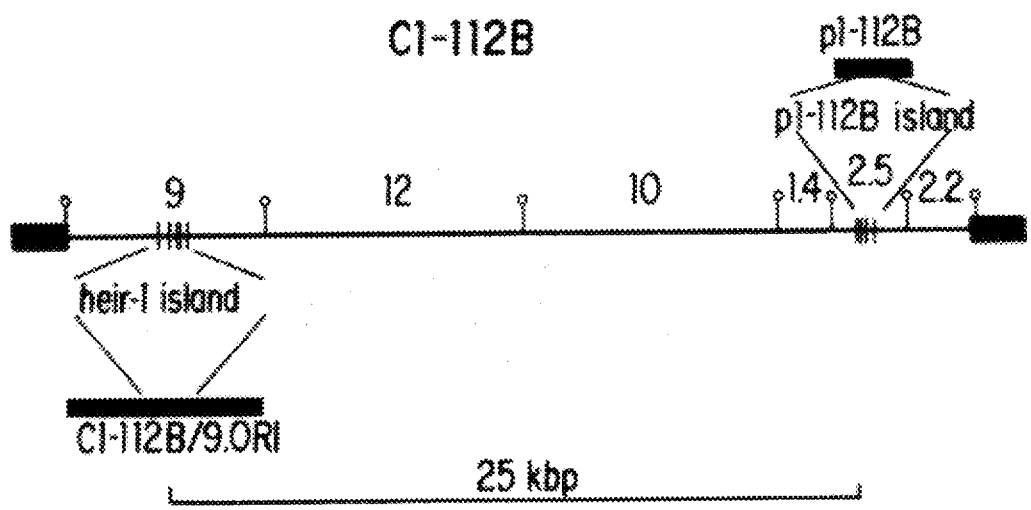
FIG. 2: Restriction map of cosmid C1-112B.

DNA Probes p1-112B is a 2.5 kbp long genomic DNA clone from a 1pter-p35-specific microclone bank (Martinsson et al., 1989). The original microclone was prepared by cloning Eco RI fragments into the lambda vector NM1149. For further use the fragment was recloned into the plasmid vector Bluescript KS+(Stratagene). p1-112B was mapped by Southern hybridisation on a series of (MouseXHuman) hybrid cell lines in the region 1pter-p36.12. C1-112B represents a cosmid clone isolated from a genomic cosmid library (see below) by means of the probe p1-112B. The insert of C1-112B is about 37 kbp long (FIG. 2). C1-112B/9.ORI is a 9.0 kbp Eco RI sub-fragment from the cosmid C1-112B (FIG. 2). In order to prepare this clone, 8 µg of C1-112B DNA was digested with the restriction enzyme Eco RI (Boehringer Mannheim) in accordance with the manufacturers instructions, fractionated by electrophoresis in a 0.6% agarose-gel and the DNA was revealed by ethidium bromide staining. An agarose fragment which contained the 9.0 kbp sub-fragment of the cosmid was excised and the DNA contained was isolated from the agarose by phenol extraction. No measurement of the concentration of the DNA obtained was carried out. The DNA was then ligated with 50 ng of Eco RI digested de-phosphorylated plasmid DNA (Bluescript KS+) in 10 µl volume in the presence of 1 unit of T4-DNA ligase (Boehringer Mannheim) and ligation buffer in accordance with the manufacturer's instructions. Ligation was carried out for 14 hours at 12° C. Then the entire ligation mixture was used to transform XL-1blue host bacteria (Stratagene). Transformation was carried out using the standard method (Sambrook et al., 1989). After the cells had been plated out onto LB-amp (LB-medium+ampicillin [50 µg/ml]) plates and incubated overnight, recombinant colonies could be isolated. Nb-1 is an Ny-myc specific genomic 1.0 kbp EcoRI/BamHI fragment, cloned in pBR322 (Schwab et al., 1983). The c-myc specific clone pMc-myc 54 is a 1.3 kbp cDNA fragment cloned in PSP64 (Darveau et al., 1985).

Radioactive Labelling of DNA and cDNA Probes

Insert fragments of the recombinant clones were used as probes for hybridisation. 5 to 8 µg of a cloned DNA were digested with restriction enzymes to separate the insert from the vector DNA, fractionated by agarose gel electrophoresis and the insert fragment in an agarose fragment was separated out. Then the DNA was separated from the agarose by phenolisation. 20–50 ng of this insert DNA were labelled with 32p-dCTP by "random priming" using the standard method (Sambrook et al., 1989) and used as hybridization probes.

Analysis of Genomic DNA

Genomic DNA from whole blood and various organ and tissue samples was isolated using standard methods (Sambrook et al., 1989), digested with restriction endonucleases in accordance with the manufacturer's instructions (Boehringer Mannheim, New England Biolabs, Promega) and fractionated by gel electrophoresis in 0.8% agarose gels. This was followed by partial depurination, denaturation and capillary transfer onto nylon membranes (GeneScreen-plus, NEN) under denaturing conditions in accordance with established methods (Sambrook et al., 1989). The membranes were air-dryed after the transfer of the DNA, incubated at 80° C. for 30 minutes and subjected to UV irradiation. For hybridisation, membranes were first pre-hybridised in 500 mM Na-phosphate buffer, pH 7.2, 7% SDS and 1 mM EDTA (68° C., 1–2 hours) and then incubated at 68° C. overnight in the same buffer with the probe, with constant agitation. The membranes were generally scrupulously washed (40 mM Na-phosphate buffer pH 7.2, 1% SDS, 68° C.), sealed in PE film whilst still damp and exposed on X-ray film (Kodak XAR-5) with intensifier film.

RNA Analyses

Total RNA from tissues and from cell culture material was isolated using the guanidium-thiocyanate method described by Chomczynski and Sacchi (1987). Poly(A)+RNA was isolated using the conventional method (Sambrook et al., 1989) by affinity chromatography using olido-d(T) columns. Poly(A)+RNA was isolated from about 2–5 mg of total RNA in each case. The yield was about 2–3% of the total RNA. For Northern analysis, from each tissue, 2 µg (normal human tissue) or 3 µg (mouse tissue and neuroblastoma culture cells) were fractionated in formaldehyde-agarose gels using the appropriate methods (Sambrook et al., 1989) and transferred onto membranes (GeneScreen, NEN). The Northern blots were hybridised using the same method as for Southern blots.

DNA Sequence Analysis

The dideoxy sequencing kit obtainable from Applied Biosystems was used.

EXAMPLE 1

Pulse Field Gel Electrophoresis

High molecular weight genomic DNA was isolated from human sperm or lymphocytes which had been enclosed in agarose blocks, using published methods (Herrmann et al., 1987). The DNA in the agarose blocks (about 10 µg/block) was digested with methylation-sensitive, rarely cutting restriction endonucleases (2–30 units per block) in accordance with the recommendations of the manufacturer (New England Biolabs, Boehringer Mannheim) by either single or double digestion. Then the agarose blocks with the digested DNA were separated in 1% agarose gels by CHEF electrophoresis in a pulsating electrical field. A PULSAPHOR™ electroporesis system (LKB) was used for this. DNA separation was carried out in 3-phase runs: Phase 1:40 s (8 h), Phase 2:15 s (8 h), Phase 3:3 s (8 h). Electrophoresis was carried out in 0.5× Tris-borate-EDTA (TBE, see Sambrook et al., 1989) at 200 V and 10° C. Subsequent Southern transfer and hybridization of membranes were carried out as described above.

Figure 1A:
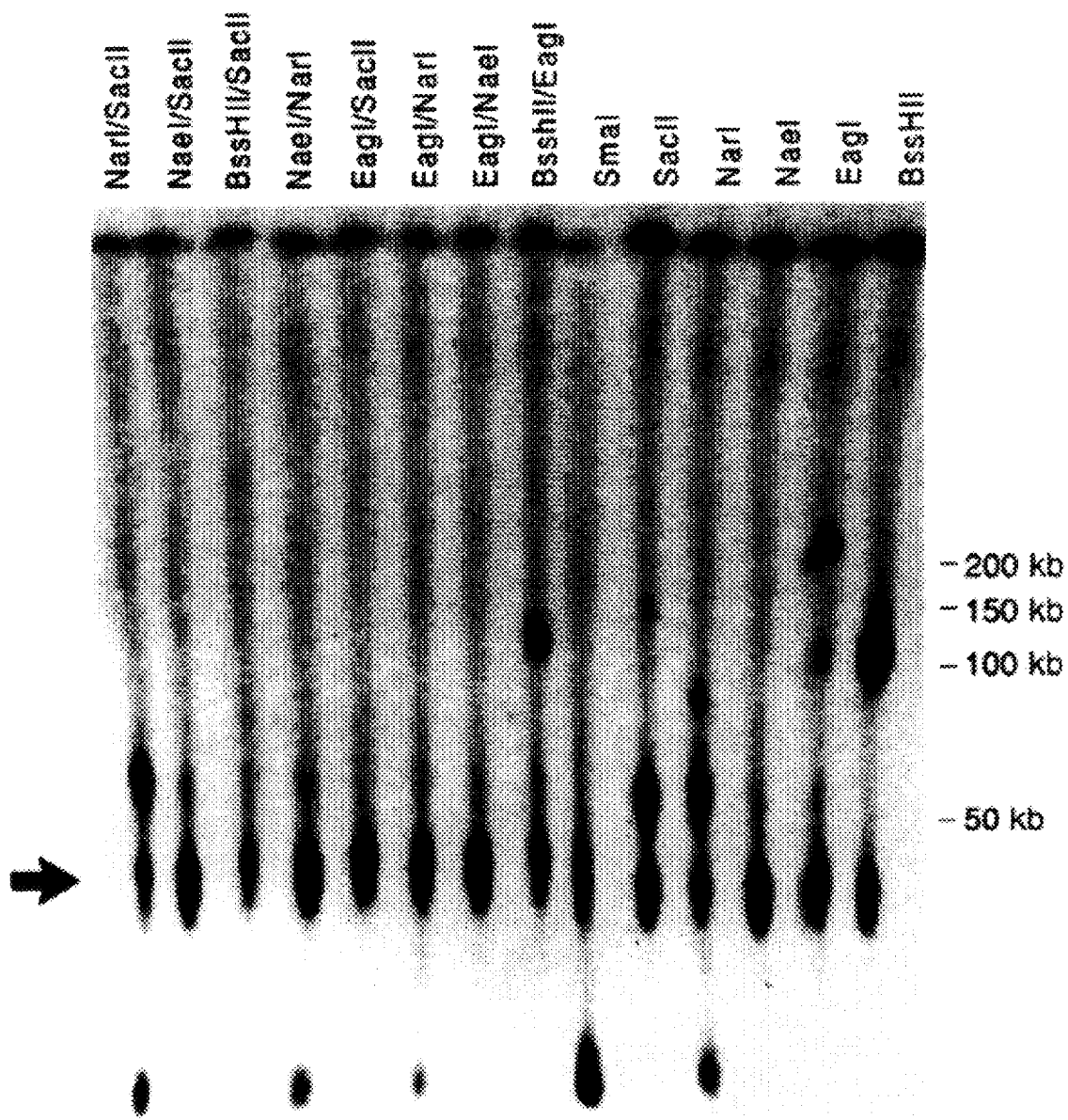
FIG. 1A and 1B.
Figure 1B:
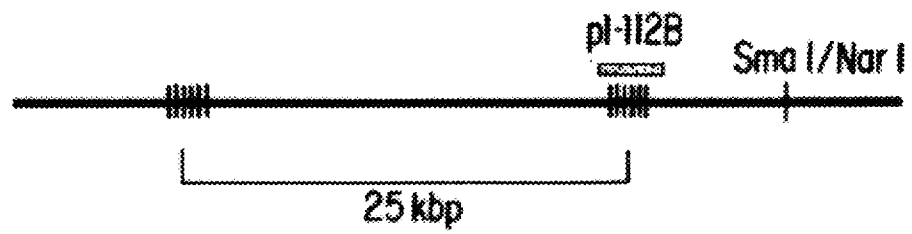

The results of the PFGE are shown in FIG. 1: A: 32p-labelled p1-112B was hybridised with a PFG blot which contained about 10 µg of normal human sperm DNA in each trace, digested with the enzymes mentioned. The fragment which represents the spacing between the two CpG Islands is marked by an arrow. The sizes of the lambda-DNA concatamers are shown in kbp as markers. The autoradiography exposure took 3 days. B: Schematic representation of the genomic region characterised by p1-112B. The probe is illustrated by a shaded horizontal bar. Two CpG Islands are indicated by a cluster of vertical bars. Additional bands detected with the probe (eg. traces NarI and SmaI in A, shown as a vertical bar in B) originate from recognition sites within the probe and represent fragments outside the section between the CpG Islands.

EXAMPLE 2 a) Manufacturing a cosmid library

High molecular weight genomic DNA was isolated from human lymphocytes: the erythrocytes were lysed from 40 ml of peripheral blood and the DNA was extracted from the lymphocytes in 20 mM tris-HCl, pH 7.6, 20 mM EDTA, 1% sarkosyl and 200 µg/ml proteinase K (Boehringer Mannheim). The DNA obtained was partially digested with the restriction enzyme Mbo I, without previous phenolization, so that on average 35–45 kbp long fragments were obtained. A concentration of fragments of this length was achieved by gel fractionation in 0.25% agarose gels.

Then the genomic DNA fragments and Bam H1-cut, dephosphorylated vector-DNA (cosmid vector pWE15, Stratagene) were ligated together in a weight ratio of 1:5. In order to do this, 5 µg of genomic fragments and 25 µg of vector DNA in a total 10 µl volume were incubated for 16 hours at 12° C. in the presence of T4-DNA ligase and ligation buffer (Boehringer Mannheim). The ligated material was packaged with an in-vitro packaging mix in infectious phage particles and used to transform E. coli NM554 cells. A yield of 2×10⁷ recombinants per µg of genomic DNA was achieved.

2.5–2.8×10⁷ recombinant bacteria from the cosmid library were plated out on LB$^{amp}$ plates measuring 22×22 cm directly on membranes (GeneScreen Plus, NEN) and incubated for 13 hours. Two copies (replica filters) were prepared from the primary colony membranes (master filters) and incubated for a further 8 hours for colony growth. The master filters were then impregnated with freezing medium (LB+20% glycerol), placed on PLEXIGLASS® glass plates and stored at −80° C. Replica filters were impregnated for 5 minutes with 0.2M NaOH, 1% SDS, 1.5M NaCl, then neutralised in 50 mM Na-phosphate buffer, pH 6.5, and air-dried.

b) Screening of the cosmid library using the probe p1-112B

Insert DNA from p1-112B was labelled by random priming (see above) and hybridized as a probe on the replica filters of the cosmid library under standard conditions (Sambrook et al., 1989). Areas with positive colonies were excised accordingly from the deep-frozen master filters, resuspended in LB medium, and plated out on filters at low density (approximately 600–1000 colonies per 85 mm of filter), incubated, and hybridized again with labelled p1-112B probe. After this step, positive signals could be attributed to individual colonies. The individual colonies were isolated and amplified in 50 ml cultures for the isolation of cosmid DNA. Cosmid DNA was prepared using standard methods (Sambrook et al., 1989).

EXAMPLE 3

Isolation of a C1-112B/9.ORI Positive cDNA from a HeLa cDNA Library 140,000 plaques from a HeLa cDNA library (Stratagene) were searched for positive cDNA plaques using the genomic sub-fragment C1-112B/9.ORI. The principle working steps for isolating cDNA clones from a cDNA library are shown as follows.

A. Primary Screening:

1. Plating out the phage.

The phages were diluted with TM in accordance with the initial titre (1.5×10¹⁰ pfu/ml) so as to obtain roughly 70,000 plaques per 22×22 cm² plate. The corresponding quantity of phage was then incubated with 4 ml of an overnight culture of XL-1 blue bacteria for 20 minutes at 37° C. Then, 40 ml of top agar (preheated to 55° C.) was added to this mixture and the mixture was plated out on an LB plate measuring 22×22 cm². The plates were then incubated overnight at 37° C.

2. Plaque transfer onto GENESCREEN-PLUS™ nylon membranes.

After overnight incubation has occurred followed by storage at 4° C. for 2 hours, the plate was covered for 2 minutes with a 21×21 cm² GENESCREEN-PLUS™ nylon membrane. Then the membrane was placed for 3 minutes on a filter paper which had been impregnated with denaturing solution (1.5 M NaCl, 0.5M NaOH). It was then incubated for 10 minutes on a filter paper impregnated with neutralizing solution. After drying in air for 1 hour and at 80° C. for 30 minutes, the DNA was fixed on the membrane by UV irradiation.

3. Hybridization of the membranes with C1-112B/9.ORI.

This step was carried out using conventional methods (Sambrook et al., 1989).

B. Secondary Screening:

Since individual plaques could not be achieved because of the high density (70,000 plaques per plate), secondary screening had to be carried out (with the purpose of isolating individual plaques).

1. Isolation of positive plaques.

The plaques which had produced positive signals in the primary screening were isolated from the large plate. In accordance with the method described in A, secondary screening was carried out. The only differences in this screening related to the size of the plates (8 cm Petri dishes) and the density of plaques per dish (150 plaques per dish; different dilutions of the positive plaque were plated out).

2. Analysis of positive individual plaques.

This was carried out using the methods currently used in laboratories, eg. in vivo excision, carried out in accordance with the instructions of Stratagene, PCR analysis, etc. (Sambrook et al. 1989).

The cDNA clone known as HEIR-1 was obtained, which has the sequence shown in SEQ ID NO: 1. The cDNA sequence obtained is also shown in FIG. 3A; the two start codons, a polyadenylation signal and the transcription termination codon are underlined and an ATTTA motif is marked by a dashed line. FIG. 3B shows a comparison of the derived amino acid sequence of HEIR-1 with the murine HLH462 protein.

C. Direct sequencing of the 5' regulatory region:

The sequence of the promoter was obtained by sequencing the clone C1-112B/9ORI. The oligonucleotide TGG GGA GTG AGT CCA GAG, shown in SEQ ID NO: 6, which is complementary to the HEIR-1 cDNA, was used as sequencing primer.

EXAMPLE 4

Transcription of the HEIR-1 Gene in Various Human Tissues

The results of the Northern hybridizations, carried out as described under "Materials and Methods", are shown in FIG. 5.

Figure 5A:
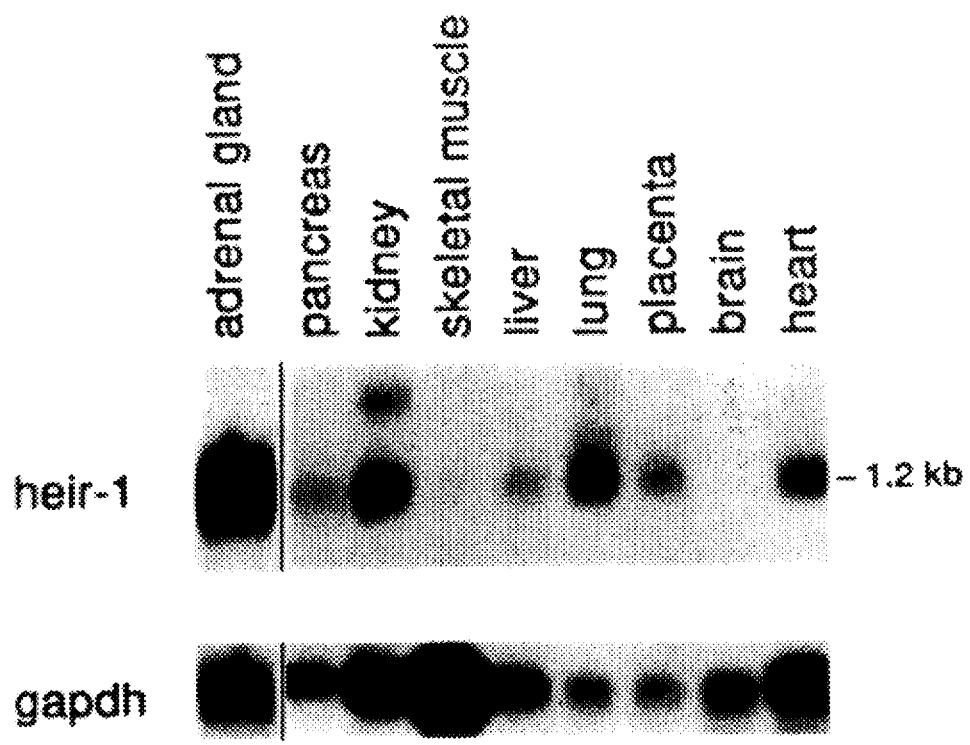
FIGS. 5A, 5B, and 5C.

FIG. 5A: Northern blots of poly(A)+RNA (2 µg) from 9 different adult tissues. The 8 traces on the left represent a so-called MTN (multiple tissue Northern), obtainable from Clontech (Palo Alto). For isolating adrenal-RNA, tissue was used which had been taken from a patient in the course of a kidney and adrenal operation. The size of the positive band is given in kb. The calibration of the quantity of RNA applied to each trace was carried out by hybridizing a glyceraldehyde-phosphate-dehydrogenase probe (GAPDH) with the blot after removing the HEIR-1 probe (shown at the bottom of the Fig.). The autoradiography exposure took 1 day (HEIR-1) or 4 hours (calibration).

Figure 5B:
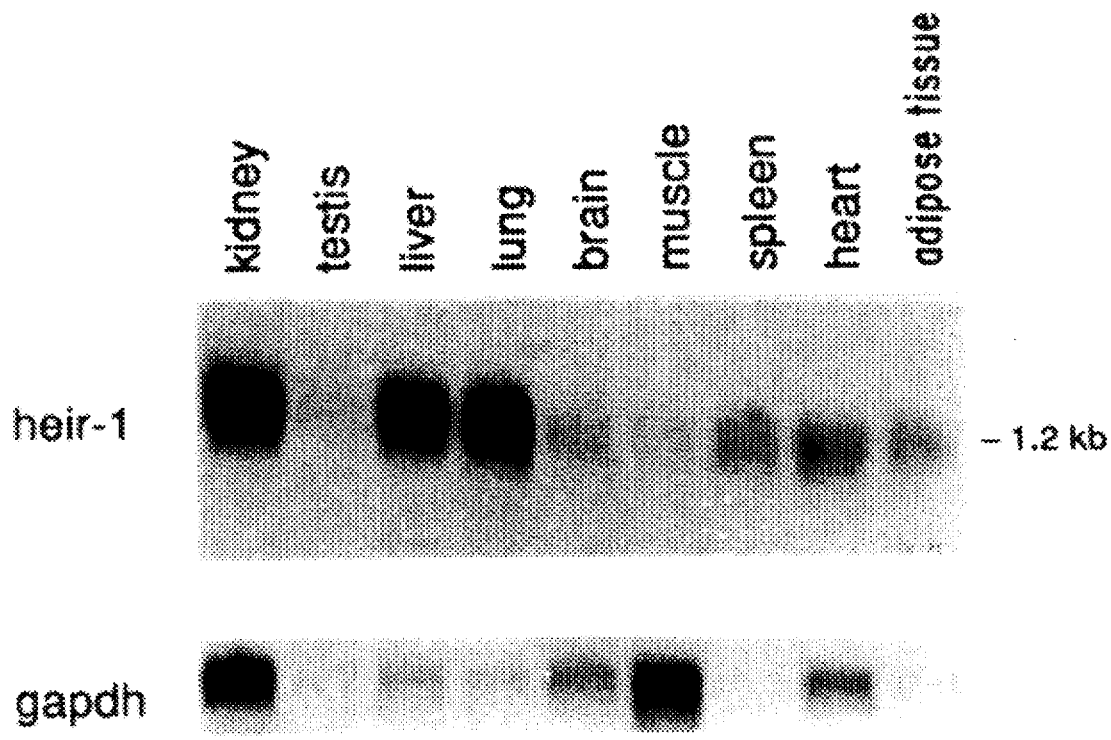

FIG. 5B: Northern blots of poly(A)+RNA (3 µg) from adult mouse tissue, hybridised with human HEIR-1, as described under A.

Figure 5C:
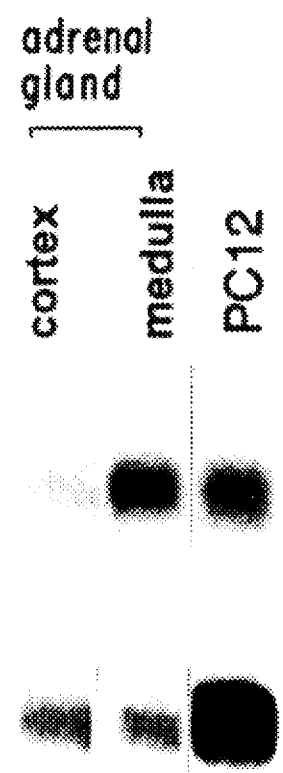

FIG. 5C: Northern hybridisation of the HEIR-1 cDNA probe with poly(A)+RNAs (for 3 µg) of cortex of bovine adrenal gland, medulla of bovine adrenal gland and rat PC12 cells. The quantities of RNA were standardized by methylene blue staining of RNA on the filter and with a rat GAPDH probe. The size of the positive band is given in kb. The autoradiograph was exposed for 2½ days (HEIR-1 on bovine RNA) and 1 day (HEIR-1 on PCT12 cells).

EXAMPLE 5

Transcription of HEIR-1 and c-myc in Neuroblastoma Cell Lines

Figure 7:
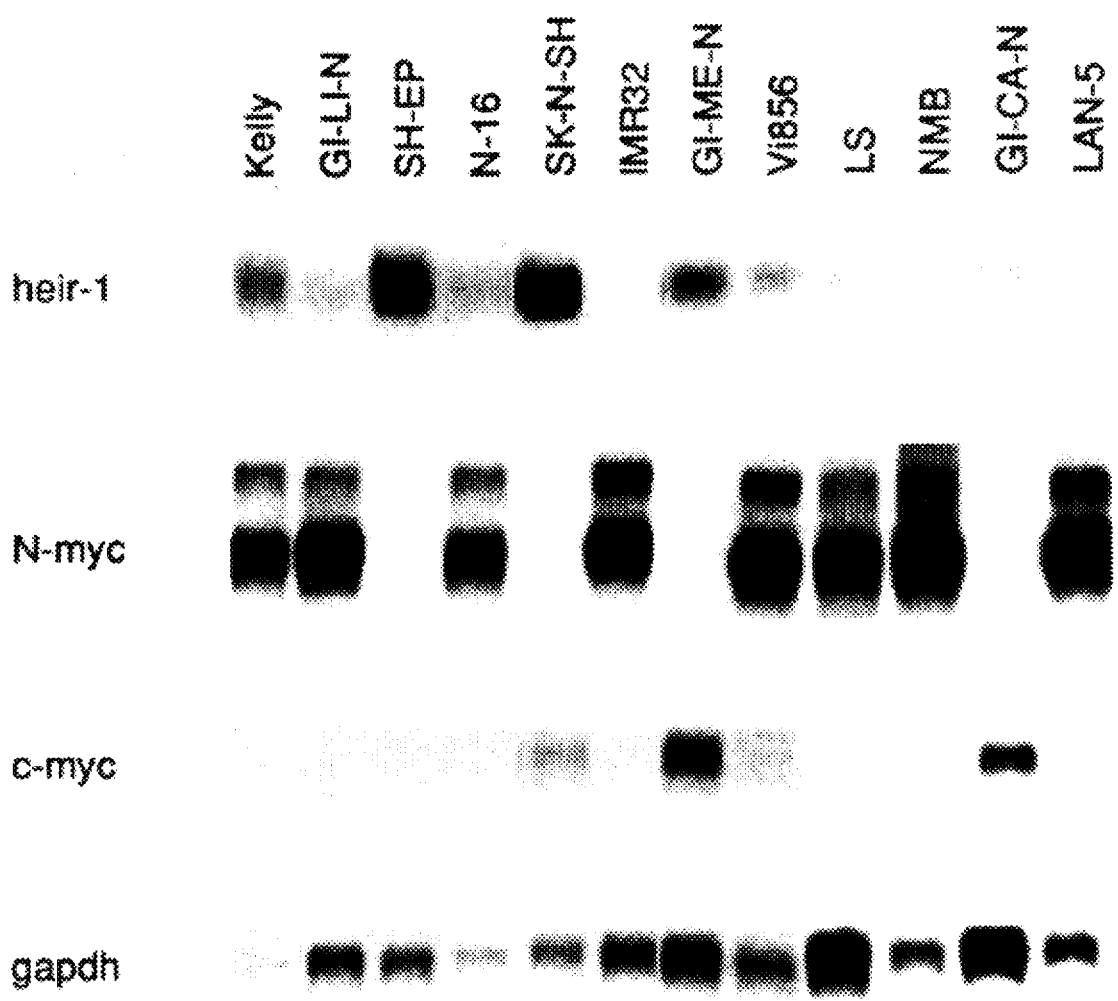
FIG. 7: Transcription of HEIR-1, N-myc and c-myc in neuroblastoma cell lines.

Northern blots containing poly(A)+RNA (3 µg/trace) from 12 different neuroblastoma cell lines were hybridised one after the other with the 3 cDNA probes specified. Calibration was carried out using the GAPDH probe (bottom trace). The autoradiography exposure took 5 to 18 hours (FIG. 7).

EXAMPLE 6

Inverse Correlation Between the Expression of HEIR-1 and N-myc in Embryonic Mouse Tissue The preparation of embryonic tissue sections and in situ hybridisations were carried out as described by Aguzzi et al., 1990. Sense and anti-sense cRNA probes were prepared by in vitro transcription of the HEIR-1 cDNA or of a mouse sub-clone corresponding to the third exon of N-myc (DePinho et al., 1986), in the presence of $^{35}$S-labelled rUTP. Sense-transcribed probes were used as control.

In situ hybridization of sections of mouse tissue embedded in paraffin, from various embryonic stages, which had been hybridized either with HEIR-1 or N-myc anti-sense probes, exhibited clearly tissue-specific signals for both. In particular, the expression of each of the genes in the developing brain was limited to various sections of the neuroectoderm. In the layer of forebrain neuroectodermal cells, N-myc was expressed predominantly in the regions of the cortex and hypothalamus. However, a sharply defined ventral part of the neuroectoderm, which comprises the cordal telencephalon and its connections to the developing diencephalon, was completely free from N-myc message. By contrast, this was the only part of the forebrain neuroectoderm which showed HEIR-1 expression. The regions which showed either HEIR-1 or N-myc expression were separated by strikingly sharp and essentially coinciding boundaries. At the boundary between the neuroectoderm and tissues of mesodermal origin there was also complementary expression of the two genes: HEIR-1 was strongly expressed in the developing skull structures, whereas N-myc in this tissue exhibited only non-specific background values.

EXAMPLE 7

Identification of a Restriction Fragment Length Polymorphism (RFLP) for the Probe HEIR-1

Genomic DNA was isolated from peripheral blood from 7 different individuals using standard methods (Sambrook et al., 1989). The collection of DNAs was digested with 40 different restriction endonucleases (Boehringer Mannheim, New England Biolabs, Promega) in accordance with the manufacturer's instructions and fractionated by gel electrophoresis in 0.8% agarose gels. Southern transfer of the fractionated DNA onto GENESCREEN nylon membranes (NEN) was carried out using the standard methods described above. The membranes were hybridised with the $^{32}$P-dCTP-labelled probe heir-1 in accordance with the standard methods mentioned, washed under conditions of high stringency (40 mM Na-phosphate buffer, pH 7.2, 1% SDS, 68° C.) and exposed for 24 hours on Kodak X-AR5 film. An RFLP was recognised by comparison of the hybridisation patterns on DNAs which had been digested with the same enzyme. The band pattern on Apa I-digested DNAs showed the occurrence of two alleles in different individuals. The size of the alleles, constant bands and allele frequency are shown in Table 1:

TABLE 1

| | RFLP for the locus HEIR-1: | | | | | |
|---|---|---|---|---|---|---|
| Fragments (kbp) | 1.0 | 0.6 | 12.0 | 6.5 | 3.2 | Frequency* |
| Allele A1 | + | − | + | + | + | 57% |
| Allele A2 | − | + | + | + | + | 43% |

*Total frequency determined after examining a total of 56 chromosomes

EXAMPLE 8

Localisation of HEIR-1 in the Neuroblastoma Consensus Deletion

A Southern blot of EcoRI-digested DNA from different (MouseXhuman) microcell hybrids and the relevant human and mouse controls was hybridised with $^{32}$P-labelled HEIR-1-cDNA. The Southern blot is shown in FIG. 6.

A: Human (10 µg): Lymphocyte DNA; Mouse (20 µg): genomic Balb/c-DNA. Hybrids (20 µg each): 8:4-BE1, total human chromosome 1; 20-EA3, del(1)(pter-p36.12); 20-DH8, del(1)(pter-p31); 20-AE2, del(1)(pter-p11). Solid vertical bars in the bottom figure show the chromosome 1 material which is contained in the hybrids, whereas shaded regions show the deletions. The probe showed a human (H) and a murine (M) band in the relevant traces.

B: Analysis of the loss of heterozygosity (LOH) at the HEIR-1 locus of the neuroblastoma patient N-29. A Southern blot containing ApaI-digested normal DNA from peripheral blood (N) and tumour (T) DNA was hybridized with the HEIR-1 probe. Normal DNA shows two bands at 1 kbp and 0.6 kbp which correspond to the two HEIR-1 alleles. The tumour DNA shows the loss of the upper allele (arrow). The consensus deletion (cons.del.) is shown as the region between the proximal break-off point of the deletion in 20-EA3 and the distal break-off point of the allelic N-29 deletion. The autoradiography exposure took 16 hours (A) and 4 days (B).

EXAMPLE 9

Loss of Heterozygosity Analysis in Neuroblastoma Tumours

Figure 8:
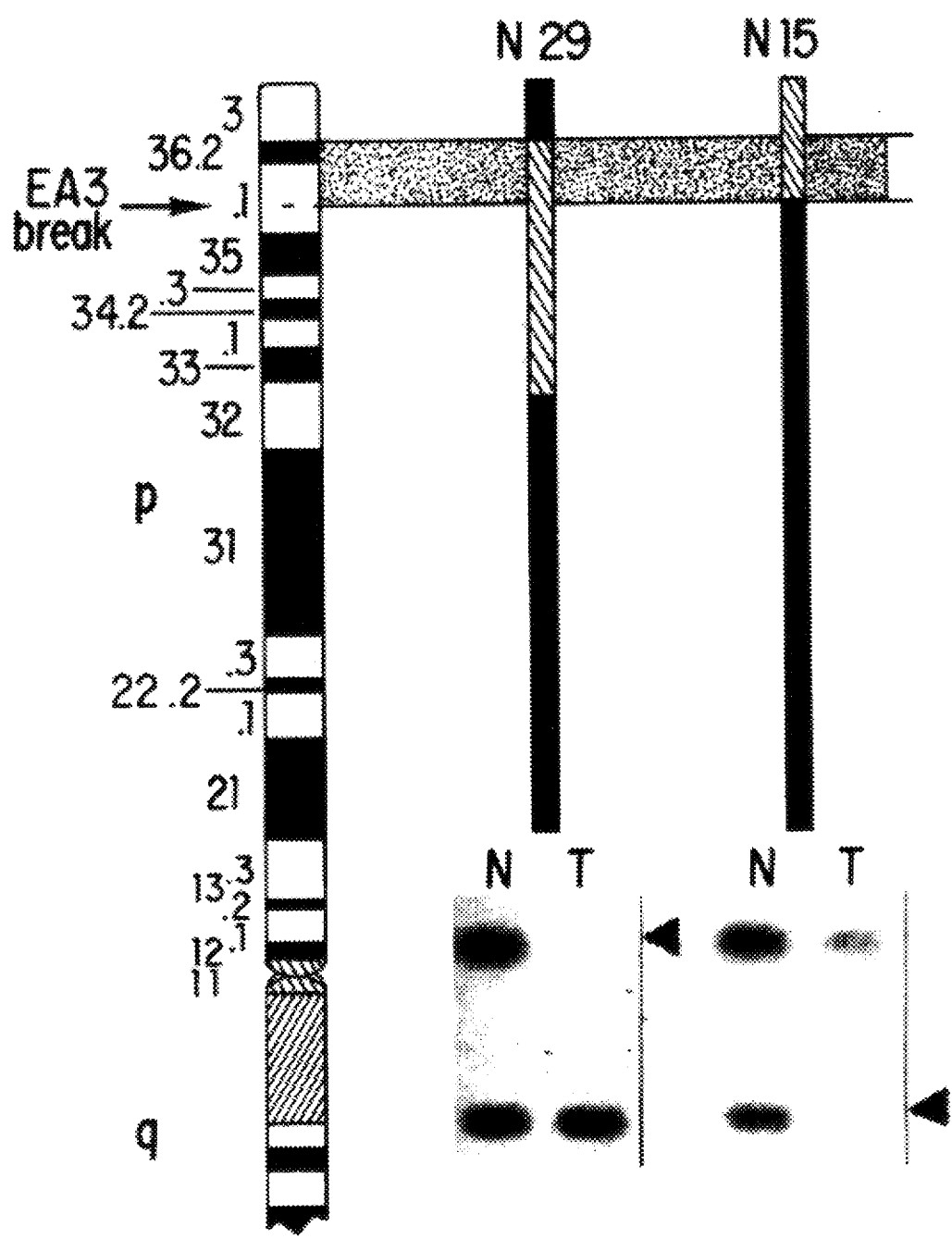
FIG. 8: LOH-analysis (Loss of Heterozygosity) of two neuroblastoma tumours (N-15, N-29) with the probe HEIR-1.

10 μg of genomic DNA from tumour tissue and corresponding normal tissue (peripheral blood) from neuroblastoma patients, prepared as described in Example 1, was cut with ApaI in accordance with the manufacturer's instructions (Boehringer Mannheim), fractionated in 0.8% agarose gels, transferred to nylon membranes and hybridised with the $^{32}$P-labelled HEIR-1 probe. Then the filters were scrupulously washed as described in Example 1 and exposed on X-ray film. The RFLP analysis is illustrated in FIG. 8 and shows the allele pattern described in Example 7 for two representative neuroblastoma patients. The residual hybridization which is visible in the tumour DNA of N-15 results from the fact that the starting material used to isolate the tumour DNA contained traces of normal tissue.

EXAMPLE 10

Expression of Recombinant HEIR-1 in E. coli

The E. coli expression plasmid pET-2a described by Studier et al., 1990 was modified by replacing the short NdeI-BamHI fragment by an oligonucleotide coding 6 histidine amino acids (Adams et al., 1992). In the 3' position relative to this oligonucleotide an HEIR-1 coding PCR fragment corresponding to the sequence shown in SEQ ID NO: 3 was cloned, taking into account the reading frame. Consequently, this bacterial expression vector (pETH-2a HEIR-1) contains sequences which code for a (His)6x-HEIR-1 fusion protein. After transformation of the E. coli strain BL21 (DE3) the protein was expressed in E. coli by induction with IPTG in accordance with the standard procedure (Sambrook et al.) and after bacterial lysis by means of nickel complex affinity chromatography (Hochuli et al., 1988) it was isolated from the bacterial extract.

EXAMPLE 11

Preparation of Polyclonal Antibodies Against HEIR-1

Figure 9:
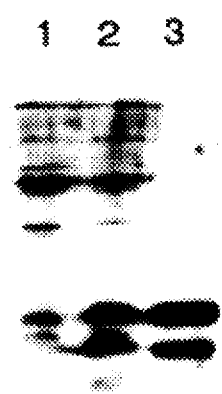
FIG. 9: Western-Blot Analysis. Detection of recombinant HEIR-1 by means of polyclonal antibodies.
Figure 4:
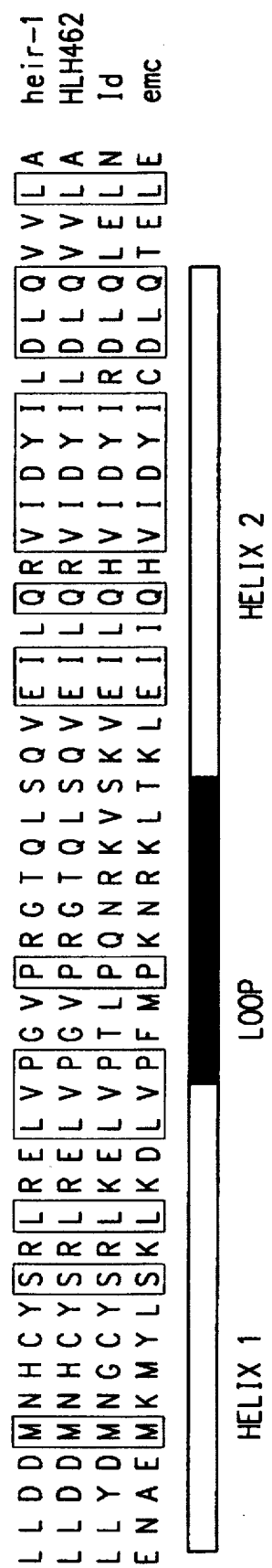
FIG. 4: Amino acid sequence comparison of the HLH motif between HEIR-1 (SEQ ID NO: 7), murine HLH562 (SEQ ID NO: 7), murine Id (SEQ ID NO: 8) and drosophilia emc (SEQ ID NO: 9)

In order to obtain antibodies a rabbit was immunized with roughly 300 μg of HEIR-1 protein (emulsified with complete Freund's adjuvant). After 2 and 5 weeks, the rabbit was immunized with approximately 100 μg HEIR-1 protein (emulsified with incomplete Freund's adjuvant) to increase the antibody concentration (booster). The serum isolated from the immunized rabbit was tested by Western blot analysis (Sambrook et al.) as shown in FIG. 9. Detection of the protein-bound antibody on the Western blot was carried out using ECL analysis (Enhanced Chemiluminescence, Amersham). In FIG. 9, the traces of the blot designated 1 and 2 represent the total bacterial protein before (1) and after (2) induction with IPTG. Trace 3 contains purified recombinant HEIR-1 fusion protein.

BIBLIOGRAPHY

Adams, B., et al., 1992, Genes & Dev. 6, 1589–1607.

Aguzzi, A., Wagner, E. F., Williams, L. R. and Courtneidge, S. A., 1990, The New Biologist 2, 533–543.

Bader, S. A., Fasching, C., Brodeur, G. M and Standbridge, E. J., 1991, Cell Growth and Diff. 2, 245–255.

Balaban-Malenbaum, G. and Gilbert, F., 1977, Science 198, 739–741.

Benezra, R., Davis, R. L., Lockshon, D., Turner, D. L. and Weintraub, H., 1990, Cell 61, 49–59.

Bernard, O., Cory, S., Gerondakis, S., Webb, E. and Adams, J. M., 1983, Embo J. 2, 2375–2383.

Biedler, J. L., Helson, L. and Spengler, B. A., 1973, Cancer Res. 33, 2643—2652.

Bird, A. P., 1986, Nature 321, 209–213.

Brawerman, G., 1989, Cell 57, 9–10.

Chomczynsky, P. and Sacchi, N., 1987, Anal. Biochem. 162, 156–159.

Christy, B. A., Sanders, L. K., Lau, L. F., Copeland, N. G., Jenkins, N. A. and Nathans, D., 1991, Proc. Nat. Acad. Sci. USA 88, 1815–1819.

Darveau, A., Pelletier J. and Sonnenberg, N., 1985, Proc. Nat. Acad. Sci. USA 82, 2315–2319.

Davis, R. L., Weintraub, H. und Lassar, A. B., 1987, Cell 51, 987–1000.

DePinho, R. A., Legouy, E., Feldman, L. B., Kohl, N. E., Yancopoulos, G. D. and Alt, F. W., 1986, Proc. Natl. Acad. Sci. USA 83, 1827–1831.

Donti, E., Longo, L., Tononi, G. P., Verdona, G., Melodia, A., Lanino, E. and Coraglia-Ferraris, P., 1988, Cancer Genet. Cytogenet. 30, 225–231.

Ellis, H. M., Spann, D. R and Posakony, J. W., 1990, Cell 61, 27–38.

Fong, C.-T., Dracopoli, N. C., White, P. S., Merril, P. T., Griffith, R. C., Housman, D. E and Brodeur, G. M., 1989, Proc. Natl. Acad. Sci. USA 86, 3753–3757.

Friend, S. H., Bernards, R. Rogelij, S., Weinberg, R. A. Papaport, J. M., Albert, D. M. and Dryja, T. P., 1986, Nature 323, 643–646.

Garell, J. and Modolell, J., 1990, Cell 61, 39–48.

Ghysen, A. and Dambly-Chaudiere, C., 1989, Trends in Genetics 5, 251–255.

Greene, L. A. and Tischler, A. S., 1976, Proc. Natl. Acad-Sci. USA 73, 2424–2428.

Harlow, E. and Lane, D., 1988, Antibodies, A Laboratory Manual, Cold Spring Harbor Laboratory.

Herrmann, B. G., Barlow, D. P. and Lehrach, H., 1987, Cell 48, 813–825.

Hochuli, E., Bannwarth, W., Döbeli, H., Gentz, R. and St über, D., 1988, Bio/Technology 6, 1321–1325. Jones, N., 1990, Cell 61, 39–48.

Köhler, G. and Milstein, C., 1975, Nature 265, 495–497.

Longo, L., Christiansen, H., Christiansen, N. M., Cornaglia-Ferraris, P. and Lampert, F., 1988, J. Cancer Res. Clin. Oncol. 114, 636–640.

Lüscher, B. and Eisenmann, R. N., 1990, Genes Dev. 4, 2025–2035.

Martinsson, T., Weith, A., Cziepluch, C. and Schwab, M., 1989, Genes Chrom. Canc. 1, 67–78.

Minth, C. D. and Dixon, J. E., 1990, J. Biol. Chem. 265, 12933–12939.

Murre, C., Schonleber McCraw, P. and Baltimore, D., 1989a, Cell 56, 777–783.

Murre, C., Schonleber McCraw, P., Vaessin, H., Caudy, M., Lan, L. Y, Jan, Y. N., Cabrera, C. V., Buskin, J. N., Hauschka, S. D., Lassar, A. B., Weintraub, H. and Baltimore, D., 1989b, Cell 58, 537–5443.

Pochedly, C., 1976, In Pochedly, C. (ed.) Neuroblastoma, Edward Arnold Ltd., London, pp. 1–34.

Rudolph, G., Schilbach-Stückle, K., Handgretinger, R., Kaiser, P. and Hameister, H., 1991, Hum. Genet. 86, 562–566.

Russell, D. S. and Rubinstein, L. J., 1989, Pathology of Tumors of the Nervous System, 5th edition, Edward Arnold Publ., London, Melbourne, Auckland.

Sambrook, J., Fritsch, E. F. and Maniatis, T., 1989, Cold Spring Harbor Laboratory Press (2.Auflage).

Schwab, M., Alitalo, K., Klempnauer, K. H., Varmus, H. E, Bishop, J. M., Gilbert, F., Brodeur, G., Goldstein, M. and Trent, J., 1983, Nature 305, 245–248.

Studier, W., Rosenberg, A. H., Dunn, J. J. and Dubendorff, J. W., 1990, Methods Enzymol. 185, 60–89.

Tumilowicz, J. J., Nichols, W. W., Cholon, J. J. and Greene, A. E., 1970, Cancer Res. 30, 2110–2118.

Weinberg, R. A., 1991, Science 254, 1138–1146.

Weith, A., Martinsson, T., Cziepluch, C., Bruederlein, S., Amler, L. C., Berthold, F. and Schwab, M., 1989, Genes, Chrom. Canc. 1, 159–166.

Zimmerman, K. A., Yancopoulos, G. D., Collum, R. G., Smith, R. K., Kohl, N. E., Denis, K. A., Nau, M. N., Witte, O. N., Toran-Allerand, D., Gee, C. E., Minna, J. D. and Alt, F. W., 1986, Nature 319, 780–783.

Zimmerman, K. and Alt, F. W., 1990, Critical Reviews in Oncogenesis 2, 75–95.

We claim:

1. A process for aiding in the diagnosis of neuroblastoma in humans associated with a consensus deletion of human chromosome region 1p36p12, comprising assaying a sample for the presence of
   a) human DNA which codes for a Helix-Loop-Helix protein (HEIR-1), wherein the nucleotide sequence of the coding region of HEIR-1 comprises the nucleotide sequence given as SEQ ID NO: 3;
   b) the RNA transcribed from said DNA; or
   c) the gene product expressed from said RNA;
wherein the absence of DNA having the nucleotide sequence of the coding region of HEIR-1 from at least one allele, or the absence of the RNA transcribed from said DNA, or the absence of the gene product expressed from said RNA, indicates that said sample
   i) comprises neuroblastoma tissue; or
   ii) comprises tissue of an individual with an increased susceptibility to neuroblastoma; or
   iii) is derived from a neuroblastoma patient, respectively.

2. A process according to claim 1, wherein the DNA is genomic.

3. A process according to claim 2, wherein the DNA comprises the sequence shown in SEQ ID NO: 5 from position 1 to position 443, in the 5' direction from the start ATG codon.

4. A process according to claim 1, wherein the process further comprises comparing samples of human DNA or RNA isolated from suspected neuroblastoma tissue to samples isolated from healthy tissue from the same individual.

5. A process according to claim 4, in which the absence of DNA having the nucleotide sequence of the coding region of HEIR-1 is determined by RFLP analysis.

6. A process according to claim 5, wherein Apa I is used to generate restriction fragments in said RFLP analysis.

7. A process according to claim 5, wherein said RFLP analysis comprises hybridizing restriction fragments with DNA comprising a sequence of SEQ ID NO: 3 or a sequence complementary to the sequence of SEQ ID NO: 3, or a fragment of SEW. ID NO: 3 or complementary sequence thereof of at least about 200 bp, and wherein said sequence, complementary sequence, or fragment specifically hybridizes to HEIR-1 nucleic acid.

8. A process according to claim 4 or 5, wherein the DNA or RNA is hybridized with a DNA fragment of at least about 200 bp of the sequence of SEQ ID NO: 3 or a sequence complementary to the sequence of SEQ ID NO: 3. and wherein said fragment specifically hybridizes to HEIR-1 nucleic acid.

9. A process for detecting the presence of either (i) human DNA which codes for a Helix-Loop-Helix protein (HEIR-1), wherein the nucleotide sequence of the coding region of HEIR-1 comprises the nucleotide sequence of SEQ ID NO: 3, (ii) the RNA transcribed from said DNA, or (iii) the gene product expressed from said RNA, comprising assaying a sample for the presence of
   a) said human DNA which codes for a Helix-Loop-Helix protein (HEIR-1), wherein the nucleotide sequence of the coding region of HEIR-1 comprises the nucleotide sequence given in SEQ ID NO: 3;
   b) the RNA transcribed from said DNA; or
   c) the gene product expressed from said RNA, respectively.

10. A process according to claim 9, wherein the sample comprises genomic DNA.

11. A process according to claim 10, wherein the genomic DNA contains the sequence shown in SEQ ID NO: 5 from position 1 to position 443, in the 5' direction from the start ATG codon.

12. A process according to claim 9, wherein the process further comprises comparing samples of DNA or RNA isolated from a suspected neuroblastoma to DNA or RNA isolated from healthy tissue from the same individual.

13. A process according to claim 12, in which the absence of DNA having the nucleotide sequence of the coding region of HEIR-1 is determined by RFLP analysis.

14. A process according to claim 13, wherein Apa I is used to generate restriction fragments in said RFLP analysis.

15. A process according to claim 12, wherein the RNA or DNA sample is hybridized with a DNA fragment of at least about 200 bp of the sequence of SEQ ID NO: 3 or a sequence complementary to the sequence of SEQ ID NO: 3, and wherein said fragment specifically hybridizes to HEIR-1 nucleic acid.

16. A process for aiding in the diagnosis of neuroblastoma in humans associated with a consensus deletion of human chromosome region 1p36p12, comprising assaying a sample for the presence of
  a) human DNA which codes for a Helix-Loop-Helix protein (HEIR-1), wherein the nucleotide sequence of the coding region of HEIR-1 comprises the nucleotide sequence of SEQ ID NO: 3;
  b) the RNA transcribed from said DNA; or
  c) the gene product expressed from said RNA;

wherein the absence of DNA having the nucleotide sequence of the coding region of HEIR-1 from at least one allele, or the absence of the RNA transcribed from said DNA, or the absence of the gene product expressed from said RNA, respectively, indicates that said sample comprises neuroblastoma tissue.

* * * * *

UNITED STATES PATENT AND TRADEMARK OFFICE
CERTIFICATE OF CORRECTION

PATENT NO. : 5,683,878

DATED : November 4, 1997

INVENTOR(S): Ellmeier *et al.*

It is certified that an error appears in the above-identified patent and that said Letters Patent is hereby corrected as shown below.

At Column 27, line 31, please delete "given as" and insert therefor --of--;

line 41, after "neuroblastoma" please insert --compared to a normal individual-- ;

line 42, please delete "derived;"

line 64, please delete "SEW" and insert therefor --SEQ--.

At Column 28, line 41, please delete "given in" and insert therefor --of--..

Signed and Sealed this

Tenth Day of March, 1998

Attest:

BRUCE LEHMAN

*Attesting Officer*    Commissioner of Patents and Trademarks

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
    ( A ) LENGTH: 982 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 37..481

( x i ) SEQUENCE DESCRIPTION: SEQ ID NO:1:

```
AGACAATTTT CAGCAGGAAG AAGTAGAAAG GATAAA ATG GAT CCT GCA CCA CGG              54
                                        Met Asp Pro Ala Pro Arg
                                         1               5

GAA CCT CAC AGC ACC TCA CTT CTT TTG GTT TTC TTT CTC TTT GGG GCA             102
Glu Pro His Ser Thr Ser Leu Leu Leu Val Phe Phe Leu Phe Gly Ala
            10                  15                  20

CCT CTG GAC TCA CTC CCC AGC ATG AAG GCG CTG AGC CCG GTG CGC GGC             150
Pro Leu Asp Ser Leu Pro Ser Met Lys Ala Leu Ser Pro Val Arg Gly
        25                  30                  35

TGC TAC GAG GCG GTG TGC TGC CTG TCG GAA CGC AGT CTG GCC ATC GCC             198
Cys Tyr Glu Ala Val Cys Cys Leu Ser Glu Arg Ser Leu Ala Ile Ala
    40                  45                  50

CGG GGC CGA GGG AAG GGC CCG GCA GCT GAG GAG CCG CTG AGC TTG CTG             246
Arg Gly Arg Gly Lys Gly Pro Ala Ala Glu Glu Pro Leu Ser Leu Leu
 55              60                  65                  70

GAC GAC ATG AAC CAC TGC TAC TCC CGC CTG CGG GAA CTG GTA CCC GGA             294
Asp Asp Met Asn His Cys Tyr Ser Arg Leu Arg Glu Leu Val Pro Gly
                75                  80                  85

GTC CCG AGA GGC ACT CAG CTT AGC CAG GTG GAA ATC CTA CAG CGC GTC             342
Val Pro Arg Gly Thr Gln Leu Ser Gln Val Glu Ile Leu Gln Arg Val
            90                  95                 100

ATC GAC TAC ATT CTC GAC CTG CAG GTA GTC CTG GCC GAG CCA GCC CCT             390
Ile Asp Tyr Ile Leu Asp Leu Gln Val Val Leu Ala Glu Pro Ala Pro
        105                 110                 115
```

```
GGA  CCC  CCT  GAT  GGC  CCC  CAC  CTT  CCC  ATC  CAG  ACA  GCC  GAG  CTC  GCT        438
Gly  Pro  Pro  Asp  Gly  Pro  His  Leu  Pro  Ile  Gln  Thr  Ala  Glu  Leu  Ala
120                           125                      130

CCG  GAA  CTT  GTC  ATC  TCC  AAC  GAC  AAA  AGG  AGC  TTT  TGC  CAC  T              481
Pro  Glu  Leu  Val  Ile  Ser  Asn  Asp  Lys  Arg  Ser  Phe  Cys  His
135                      140                      145

GACTCGGCCG  TGTCCTGACA  CCTCCAGAAC  GCAGGTGCTG  GCGCCCGTTC  TGCCTGGGAC              541
CCCGGGAACC  TCTCCTGCCG  GAAGCCGGAC  GGCAGGGATG  GGCCCCAACT  TCGCCCTGCC              601
CACTTGACTT  CACCAAATCC  CTTCCTGGAG  ACTGAACCTG  GTGCTCAGGA  GCGAAGGACT              661
GTGAACTTGT  GGCCTGAAGA  GCCAGAGCTA  GCTCTGGCCA  CCAGCTGGGC  GACGTCACCC              721
TGCTCCCACC  CCACCCCAAG  TTCTAAGGTC  TTTTCAGAGC  GTGGAGGTGT  GGAAGGAGTG              781
GCTGCTCTCC  AAACTATGCC  AAGGCGGCGG  CAGAGCTGGT  CTTCTGGTCT  CCTTGGAGAA              841
AGGTTCTGTT  GCCCTGATTT  ATGAACTCTA  TAATAGAGTA  TATAGGTTTT  GTACCTTTTT              901
TACAGGAAGG  TGACTTTCTG  TAACAATGCG  ATGTATATTA  AACTTTTTAT  AAAAGTTAAC              961
ATTTTGCATA  ATAAACGATT  T                                                           982
```

(2) INFORMATION FOR SEQ ID NO:2:

(i) SEQUENCE CHARACTERISTICS:
        (A) LENGTH: 148 amino acids
        (B) TYPE: amino acid
        (D) TOPOLOGY: linear (ii) MOLECULE TYPE: protein (xi) SEQUENCE DESCRIPTION: SEQ ID NO:2:

```
Met  Asp  Pro  Ala  Pro  Arg  Glu  Pro  His  Ser  Thr  Ser  Leu  Leu  Leu  Val
1                   5                   10                      15

Phe  Phe  Leu  Phe  Gly  Ala  Pro  Leu  Asp  Ser  Leu  Pro  Ser  Met  Lys  Ala
               20                      25                      30

Leu  Ser  Pro  Val  Arg  Gly  Cys  Tyr  Glu  Ala  Val  Cys  Cys  Leu  Ser  Glu
          35                      40                      45

Arg  Ser  Leu  Ala  Ile  Ala  Arg  Gly  Arg  Gly  Lys  Gly  Pro  Ala  Ala  Glu
     50                      55                      60

Glu  Pro  Leu  Ser  Leu  Leu  Asp  Asp  Met  Asn  His  Cys  Tyr  Ser  Arg  Leu
65                       70                      75                       80

Arg  Glu  Leu  Val  Pro  Gly  Val  Pro  Arg  Gly  Thr  Gln  Leu  Ser  Gln  Val
                85                      90                      95

Glu  Ile  Leu  Gln  Arg  Val  Ile  Asp  Tyr  Ile  Leu  Asp  Leu  Gln  Val  Val
               100                     105                     110

Leu  Ala  Glu  Pro  Ala  Pro  Gly  Pro  Pro  Asp  Gly  Pro  His  Leu  Pro  Ile
          115                     120                     125

Gln  Thr  Ala  Glu  Leu  Ala  Pro  Glu  Leu  Val  Ile  Ser  Asn  Asp  Lys  Arg
     130                     135                     140

Ser  Phe  Cys  His
145
```

(2) INFORMATION FOR SEQ ID NO:3:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: cDNA ( i x ) FEATURE:
    ( A ) NAME/KEY: CDS
    ( B ) LOCATION: 1..357

( x i ) SEQUENCE DESCRIPTION: SEQ ID NO:3:

```
ATG AAG GCG CTG AGC CCG GTG CGC GGC TGC TAC GAG GCG GTG TGC TGC    48
Met Lys Ala Leu Ser Pro Val Arg Gly Cys Tyr Glu Ala Val Cys Cys
 1               5                  10                  15

CTG TCG GAA CGC AGT CTG GCC ATC GCC CGG GGC CGA GGG AAG GGC CCG    96
Leu Ser Glu Arg Ser Leu Ala Ile Ala Arg Gly Arg Gly Lys Gly Pro
             20                  25                  30

GCA GCT GAG GAG CCG CTG AGC TTG CTG GAC GAC ATG AAC CAC TGC TAC   144
Ala Ala Glu Glu Pro Leu Ser Leu Leu Asp Asp Met Asn His Cys Tyr
         35                  40                  45

TCC CGC CTG CGG GAA CTG GTA CCC GGA GTC CCG AGA GGC ACT CAG CTT   192
Ser Arg Leu Arg Glu Leu Val Pro Gly Val Pro Arg Gly Thr Gln Leu
     50                  55                  60

AGC CAG GTG GAA ATC CTA CAG CGC GTC ATC GAC TAC ATT CTC GAC CTG   240
Ser Gln Val Glu Ile Leu Gln Arg Val Ile Asp Tyr Ile Leu Asp Leu
 65                  70                  75                  80

CAG GTA GTC CTG GCC GAG CCA GCC CCT GGA CCC CCT GAT GGC CCC CAC   288
Gln Val Val Leu Ala Glu Pro Ala Pro Gly Pro Pro Asp Gly Pro His
                 85                  90                  95

CTT CCC ATC CAG ACA GCC GAG CTC GCT CCG GAA CTT GTC ATC TCC AAC   336
Leu Pro Ile Gln Thr Ala Glu Leu Ala Pro Glu Leu Val Ile Ser Asn
             100                 105                 110

GAC AAA AGG AGC TTT TGC CAC TGA                                   360
Asp Lys Arg Ser Phe Cys His
             115
```

( 2 ) INFORMATION FOR SEQ ID NO:4:

( i ) SEQUENCE CHARACTERISTICS:
        ( A ) LENGTH: 119 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Lys Ala Leu Ser Pro Val Arg Gly Cys Tyr Glu Ala Val Cys Cys
 1               5                  10                  15

Leu Ser Glu Arg Ser Leu Ala Ile Ala Arg Gly Arg Gly Lys Gly Pro
             20                  25                  30

Ala Ala Glu Glu Pro Leu Ser Leu Leu Asp Asp Met Asn His Cys Tyr
         35                  40                  45

Ser Arg Leu Arg Glu Leu Val Pro Gly Val Pro Arg Gly Thr Gln Leu
     50                  55                  60

Ser Gln Val Glu Ile Leu Gln Arg Val Ile Asp Tyr Ile Leu Asp Leu
 65                  70                  75                  80

Gln Val Val Leu Ala Glu Pro Ala Pro Gly Pro Pro Asp Gly Pro His
                 85                  90                  95

Leu Pro Ile Gln Thr Ala Glu Leu Ala Pro Glu Leu Val Ile Ser Asn
             100                 105                 110

Asp Lys Arg Ser Phe Cys His
             115
```

( 2 ) INFORMATION FOR SEQ ID NO:5:

( i ) SEQUENCE CHARACTERISTICS:
        ( A ) LENGTH: 446 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

| | | | | | | |
|---|---|---|---|---|---|---|
| TTTATGACCT | CGGAGGAGCT | GTGGGCTCGA | ACCAGTGTTG | GGCTAAAGGC | GACTGGCAGG | 60 |
| GGGCAGGGAA | GCTCAAAGAT | CTGGGGTGCT | GCCAGGAAAA | AGCAAATTCT | GAAAGTTAAT | 120 |
| GGTTTTGAGT | GATTTTTAAA | TCCTTGCTGC | CGGAGAGACC | CACCTCTCCC | CGGTATCAGC | 180 |
| ACTTCCTCAT | TCTTTGTATC | CACGGCTCCG | CGGTCTTCGG | CGTCAGACCA | GCCGGAGGAA | 240 |
| GCCTGTTTGC | AATTTAAGCG | GGCTGTGTAC | ACCCAGGGCC | GACGGGGGCG | GGGCCGAGGG | 300 |
| CGGGCCATTT | TGAATAAAGA | GGCGTGCCTT | CCAGGCAGGC | TCTATAAGTG | ACCGCCGCGG | 360 |
| GCACGTGCGC | CGTGCAGGTC | ACTGTAGCGG | GACTTCTTTT | GGTTTCTTT | CTCTTTGGGG | 420 |
| CACCTCTGGA | CTCACTCCCC | AGCATG | | | | 446 |

( 2 ) INFORMATION FOR SEQ ID NO:6:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:6:

TGGGGAGTGA GTCCAGAG                                                18

( 2 ) INFORMATION FOR SEQ ID NO:7:

( i ) SEQUENCE CHARACTERISTICS:
( A ) LENGTH: 46 amino acids
( B ) TYPE: amino acid
( C ) STRANDEDNESS: Not Relevant
( D ) TOPOLOGY: linear ( i i ) MOLECULE TYPE: peptide ( x i ) SEQUENCE DESCRIPTION: SEQ ID NO:7:

Leu Leu Asp Asp Met Asn His Cys Tyr Ser Arg Leu Arg Glu Leu Val
1               5                   10                  15

Pro Gly Val Pro Arg Gly Thr Gln Leu Ser Gln Val Glu Ile Leu Gln
            20                  25                  30

Arg Val Ile Asp Tyr Ile Leu Asp Leu Gln Val Val Leu Ala
            35                  40                  45

( 2 ) INFORMATION FOR SEQ ID NO:8:

( i ) SEQUENCE CHARACTERISTICS:
( A ) LENGTH: 46 amino acids
( B ) TYPE: amino acid
( C ) STRANDEDNESS: Not Relevant
( D ) TOPOLOGY: linear ( i i ) MOLECULE TYPE: peptide ( x i ) SEQUENCE DESCRIPTION: SEQ ID NO:8:

Leu Leu Tyr Asp Met Asn Gly Cys Tyr Ser Arg Leu Lys Glu Leu Val
1               5                   10                  15

Pro Thr Leu Pro Gln Asn Arg Lys Val Ser Lys Val Glu Ile Leu Gln
            20                  25                  30

His Val Ile Asp Tyr Ile Arg Asp Leu Gln Leu Glu Leu Asn (2) INFORMATION FOR SEQ ID NO:9:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:9:

```
Glu Asn Ala Glu Met Lys Met Tyr Leu Ser Lys Leu Lys Asp Leu Val
  1               5                  10                  15

Pro Phe Met Pro Lys Asn Arg Lys Leu Thr Lys Leu Glu Ile Ile Gln
             20                  25                  30

His Val Ile Asp Tyr Ile Cys Asp Leu Gln Thr Glu Leu Glu
         35                  40                  45
```